United States Patent
Horton et al.

(10) Patent No.: US 9,649,165 B2
(45) Date of Patent: May 16, 2017

(54) MEDICAL DEVICE IDENTIFIER

(71) Applicants: Board of Regents, The University of Texas System, Austin, TX (US); Cardiac Innovation, LLC., Austin, TX (US)

(72) Inventors: Rodney P. Horton, Austin, TX (US); John Anthony Pearce, Austin, TX (US); Jonathan Walker Valvano, Austin, TX (US)

(73) Assignees: Cardiac Innovation, LLC, Austin, TX (US); Board Of Regents, The University Of Texas System, Austin, TX (US)

( * ) Notice: Subject to any disclaimer, the term of this patent is extended or adjusted under 35 U.S.C. 154(b) by 571 days.

(21) Appl. No.: 13/942,465

(22) Filed: Jul. 15, 2013

(65) Prior Publication Data

US 2014/0019076 A1    Jan. 16, 2014

Related U.S. Application Data

(60) Provisional application No. 61/672,170, filed on Jul. 16, 2012.

(51) Int. Cl.
*H04W 12/00* (2009.01)
*H04M 3/00* (2006.01)
(Continued)

(52) U.S. Cl.
CPC ............. *A61B 19/44* (2013.01); *A61B 5/74* (2013.01); *A61B 90/90* (2016.02); *A61N 1/3718* (2013.01);
(Continued)

(58) Field of Classification Search
None
See application file for complete search history.

(56) References Cited

U.S. PATENT DOCUMENTS

| | | | |
|---|---|---|---|
| 5,456,692 A | 10/1995 | Smith, Jr. et al. | |
| 5,725,559 A * | 3/1998 | Alt | A61N 1/37211 128/903 |

(Continued)

FOREIGN PATENT DOCUMENTS

| | | |
|---|---|---|
| WO | 03/095024 A2 | 11/2003 |
| WO | 2004/030757 A1 | 4/2004 |

(Continued)

OTHER PUBLICATIONS

Lee, Youbok, "RFID Coil Design", Microchip Technology, Inc., 2002, [retrieved on Sep. 24, 2013] 30 pages. Retrieved from http://ww1.microchip.com/downloads/en/AppNotes/00678b.pdf.

(Continued)

*Primary Examiner* — Edward Cosimano
(74) *Attorney, Agent, or Firm* — Parker Highlander PLLC

(57) ABSTRACT

A medical device identifier can identify an implanted medical device. In one example arrangement, the medical device identifier sends electromagnetic signals to the implanted device according to one or more stored digitized waveforms. The device then senses any returned electromagnetic signals, and identifies the implanted device based on the returned electromagnetic signals. The medical device identifier may generate the electromagnetic signals from the stored digitized waveforms using an analog-to-digital converter, and may compare the returned electromagnetic signals with one or more stored digital templates corresponding to different device manufacturers. The comparison may be performed using cross correlation. In another aspect, a portal device includes an identification subsystem for identifying the provider of a medical device, and a communication (Continued)

subsystem for establishing two-way communication a call center servicing medical devices from an identified provider. The portal device may relay information between the medical device and the identified provider.

18 Claims, 16 Drawing Sheets

(51) Int. Cl.
| | |
|---|---|
| *H04L 13/02* | (2006.01) |
| *G06F 17/40* | (2006.01) |
| *G06F 19/00* | (2011.01) |
| *A61B 19/00* | (2006.01) |
| *A61N 1/37* | (2006.01) |
| *A61B 90/90* | (2016.01) |
| A61B 1/00 | (2006.01) |
| A61B 5/00 | (2006.01) |
| H03M 3/00 | (2006.01) |
| A61N 1/372 | (2006.01) |
| H04B 1/401 | (2015.01) |

(52) U.S. Cl.
CPC ..... *A61N 1/37235* (2013.01); *A61N 1/37252* (2013.01); *G06F 19/3406* (2013.01); *H04W 12/00* (2013.01); A61B 1/00112 (2013.01); A61B 5/00 (2013.01); A61B 2562/08 (2013.01); A61N 1/3727 (2013.01); A61N 1/37288 (2013.01); G06F 17/40 (2013.01); G06F 19/00 (2013.01); G06F 19/3481 (2013.01); H03M 3/00 (2013.01); H04B 1/401 (2013.01); H04L 13/02 (2013.01); H04M 3/00 (2013.01)

(56) References Cited

U.S. PATENT DOCUMENTS

| | | | |
|---|---|---|---|
| 6,073,049 A | 6/2000 | Alt et al. | |
| 6,088,618 A | 7/2000 | Kerver | |
| 6,157,859 A * | 12/2000 | Alt .................... | A61N 1/37211 607/4 |
| 6,482,154 B1 | 11/2002 | Haubrich et al. | |
| 6,978,182 B2 | 12/2005 | Mazar et al. | |
| 7,209,790 B2 | 4/2007 | Thompson et al. | |
| 7,333,013 B2 | 2/2008 | Berger | |
| 7,535,860 B2 * | 5/2009 | Park .................... | H04L 5/0048 370/204 |
| 7,586,836 B2 * | 9/2009 | Park .................... | H04L 27/262 370/209 |
| 7,751,304 B2 * | 7/2010 | Ro ...................... | H04B 1/69 370/203 |
| 7,751,306 B2 * | 7/2010 | Bune .................. | H04L 5/0048 370/203 |
| 7,885,249 B2 * | 2/2011 | Inagaki ............... | H04L 45/02 370/350 |
| 7,932,825 B2 * | 4/2011 | Berger ............... | 340/10.5 |
| 8,213,986 B2 * | 7/2012 | Inagaki ............... | H04L 45/02 455/556.1 |
| 8,280,306 B2 * | 10/2012 | Oba .................. | H04L 63/0492 455/41.2 |
| 8,326,225 B2 * | 12/2012 | Oba .................. | H04M 1/7253 455/41.2 |
| 8,331,986 B2 * | 12/2012 | Inagaki ............... | H04L 45/02 455/556.1 |
| 8,538,334 B2 * | 9/2013 | Inagaki ............... | H04L 45/02 455/41.2 |
| 8,798,542 B2 * | 8/2014 | Oba .................. | H04L 63/0492 455/41.2 |
| 8,805,526 B2 * | 8/2014 | Carpenter ........... | A61N 1/3727 607/60 |
| 9,026,219 B2 * | 5/2015 | Doerr ................ | A61N 1/37235 607/115 |
| 9,287,937 B2 * | 3/2016 | Oba .................. | H04L 63/0492 |
| 2004/0077313 A1 * | 4/2004 | Oba .................. | H04L 63/0492 455/41.2 |
| 2004/0257979 A1 * | 12/2004 | Ro ...................... | H04L 27/2613 370/208 |
| 2004/0257981 A1 * | 12/2004 | Ro ...................... | H04L 5/0048 370/210 |
| 2004/0259499 A1 * | 12/2004 | Oba .................. | H04M 1/7253 455/41.2 |
| 2005/0025117 A1 * | 2/2005 | Inagaki ............... | H04L 45/02 370/350 |
| 2005/0094550 A1 * | 5/2005 | Huh .................... | H04L 5/0007 370/203 |
| 2005/0099939 A1 * | 5/2005 | Huh .................... | H04L 27/2626 370/210 |
| 2005/0226141 A1 * | 10/2005 | Ro ...................... | H04B 1/69 370/203 |
| 2005/0247319 A1 * | 11/2005 | Berger ............... | 128/898 |
| 2006/0007850 A1 * | 1/2006 | Park .................... | H04L 5/0048 370/209 |
| 2006/0018251 A1 * | 1/2006 | Park .................... | H04L 27/262 370/209 |
| 2007/0127362 A1 * | 6/2007 | Bune .................. | H04L 5/0048 370/208 |
| 2007/0260293 A1 | 11/2007 | Carpenter et al. | |
| 2008/0048855 A1 * | 2/2008 | Berger ............... | 340/539.12 |
| 2010/0114242 A1 | 5/2010 | Doerr et al. | |
| 2011/0117849 A1 * | 5/2011 | Inagaki ............... | H04L 45/02 455/41.2 |
| 2012/0116476 A1 | 5/2012 | Kothandaraman | |
| 2012/0244855 A1 * | 9/2012 | Inagaki ............... | H04L 45/02 455/426.1 |
| 2013/0017790 A1 * | 1/2013 | Oba .................. | H04L 63/0492 455/41.2 |
| 2013/0095762 A1 * | 4/2013 | Inagaki ............... | H04L 45/02 455/41.2 |
| 2014/0225716 A1 * | 8/2014 | Oba .................. | H04L 63/0492 340/10.6 |

FOREIGN PATENT DOCUMENTS

| | | | |
|---|---|---|---|
| WO | WO-2004030757 | A1 | 4/2004 |
| WO | 2005/053786 | A2 | 6/2005 |
| WO | WO-2005053786 | A2 | 6/2005 |
| WO | 2008/069829 | A1 | 6/2008 |
| WO | 2008/106138 | A1 | 9/2008 |
| WO | 2010/062988 | A2 | 6/2010 |

OTHER PUBLICATIONS

Partial International Search Report of PCT/US2013/050604, mailed on Nov. 21, 2013, 3 pages.

International Search Report and Written Opinion of PCT/US2013/050604, mailed on Feb. 25, 2014, 20 pages.

* cited by examiner

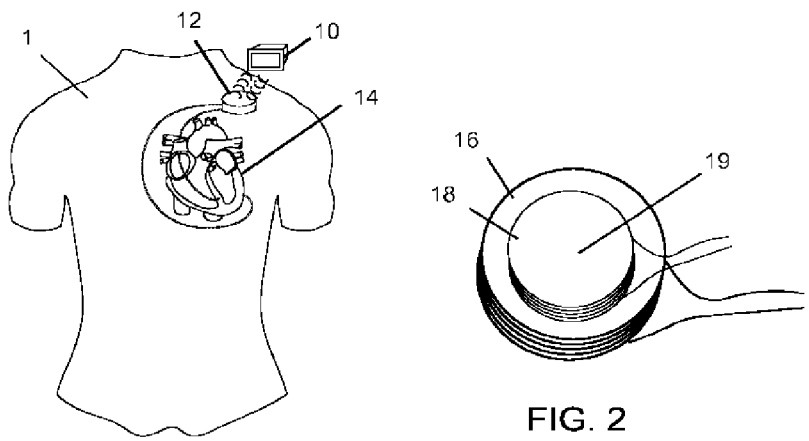
FIG. 1
FIG. 2
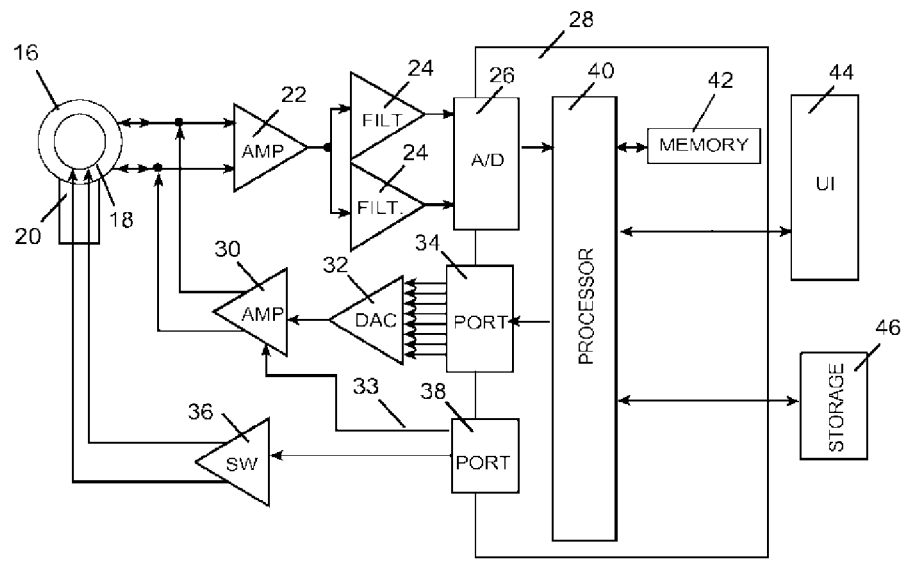
FIG. 3

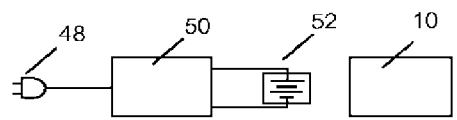
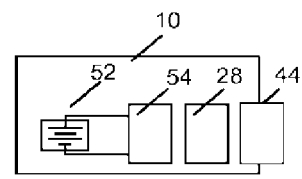
FIG. 4A        FIG. 4B
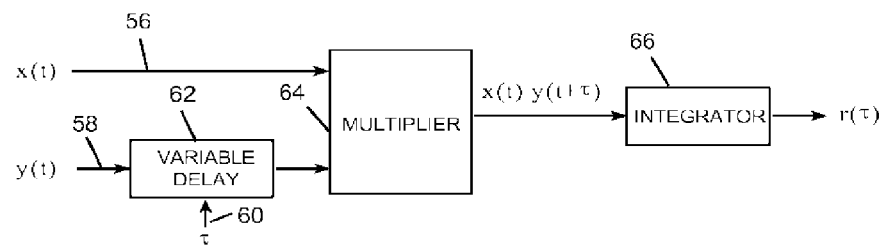
FIG. 5

US 9,649,165 B2

MEDICAL DEVICE IDENTIFIER

CROSS-REFERENCE TO RELATED APPLICATIONS

This application claims the benefit of U.S. Provisional Patent Application No. 61/672,170 filed Jul. 16, 2012 and titled "Medical Device Identifier", the entire disclosure of which is hereby incorporated by reference herein.

BACKGROUND OF THE INVENTION

Implantable medical devices are increasingly common. For example, many people now have implanted pacemakers, cardioverters, or other devices that monitor the user's heart function and automatically intervene when necessary to stimulate the heart to maintain a proper heart rhythm. Many modern implantable medical devices are externally programmable using a "programmer" that exchanges electromagnetic signals with the implanted device. The programmer may gather information stored in the implanted device, and may also be used by a physician to change operational parameters of the implanted device to tailor the operation of the device to the needs of the particular patient.

Typically, the programmer emits an electromagnetic signal that is detected by the implanted device. Upon recognizing the signal from the programmer, the device responds with its own electromagnetic signal, and the programmer and the device can thus establish two-way communication. For some devices, a constant magnetic field is used to signal the implanted device to communicate. There are a number of manufacturers of implantable medical devices. For example, there are currently five manufacturers of implantable cardiac pacemakers. Each manufacturer uses a different protocol for communicating with its device, and therefore a programmer from one manufacturer cannot be used to communicate with an implanted device from another manufacturer.

A commonly occurring problem arises when a patient having an implanted medical device such as a pacemaker arrives at an emergency room in need of emergency medical treatment. Proper treatment of the patient may require reprogramming the pacemaker. While it may be clear that the patient has an implanted pacemaker, the make and model of the pacemaker may not be readily apparent. Until the manufacturer of the device is identified, it is not known how to communicate with the pacemaker. Even if programmers for all makes of pacemakers are at hand, trying all of them in sequence takes valuable time and may not successfully identify the manufacturer. In this situation, the emergency room personnel often order a chest x-ray from which the pacemaker can be identified. However, this process also takes considerable time, and may delay treatment to the detriment of the patient.

In order to facilitate prompt and thorough patient treatment, implantable device manufacturers typically provide personnel who are on call near medical facilities to assist with any device-related issues. An emergency room physician may call a device manufacturer's representative to assist in treatment of a patient who has a pacemaker made by that manufacturer, for example to assist in any reprogramming of the device. In some cases, when a device is misidentified, the wrong manufacturer's representative is called, resulting in additional delay while the correct manufacturer's representative is called.

The cost of providing a network of on-call representatives is burdensome on the device manufacturers, and may deter manufacturers from entering new markets, especially markets having sparse populations.

BRIEF SUMMARY OF THE INVENTION

According to one aspect, a medical device identifier includes a coil and a computer subsystem. The computer subsystem includes a processor and memory, the memory holding instructions executable by the processor and also holding a plurality of digitized waveforms. The medical device identifier further includes a digital-to-analog converter coupled to the processor, drive circuitry coupled to the coil and the digital-to-analog converter, and receiver circuitry coupled to the coil and the computer subsystem. The instructions, when executed by the processor, cause the medical device identifier to sequentially excite the coil, via the digital-to-analog converter and the drive circuitry, to generate electromagnetic waveforms corresponding to one or more of the digitized waveforms. The medical device identifier also receives and digitizes, via the coil and the receiver circuitry, a returned electromagnetic waveform transmitted from a medical device in response to the electromagnetic waveforms generated by the medical device identifier, and identifies the medical device based on the digitized returned electromagnetic waveform. In some embodiments, the memory further holds a plurality of digital templates corresponding to different medical devices, and the instructions, when executed by the processor, cause the medical device identifier to identify the medical device based on a comparison of the digitized returned electromagnetic waveform with the plurality of digital templates. In some embodiments, the comparison of the digitized returned electromagnetic waveform with a respective one of the digital templates comprises a cross-correlation of the digitized returned electromagnetic waveform with the respective digital template. In some embodiments, the instructions, when executed by the processor, cause the medical device identifier to compare the digitized returned electromagnetic waveform with at least two of the plurality of digital templates, and identify the medical device based on the template best matching the digitized returned electromagnetic waveform. The medical device identifier may further produce a constant magnetic field to attempt to prompt a response from the medical device. In some embodiments, the instructions, when executed by the processor, cause the medical device identifier to, for each respective electromagnetic waveform generated, place the coil in a receive mode and digitize the output of the coil, wherein for a particular one of the generated electromagnetic waveforms the digitized output of the coil is the digitized returned electromagnetic waveform.

According to another aspect, a medical device identifier includes a coil and a computer subsystem. The computer subsystem further includes a processor and memory, the memory holding instructions executable by the processor and holding a plurality of digital templates corresponding to different medical devices. The medical device identifier further includes drive circuitry coupled to the coil and the computer subsystem, and receiver circuitry coupled to the coil and the computer subsystem. The instructions, when executed by the processor, cause the medical device identifier to sequentially excite the coil via the drive circuitry to generate electromagnetic waveforms corresponding to a plurality of digitally predefined waveforms, receive and digitize via the coil and the receiver circuitry a returned electromagnetic waveform transmitted from a medical device in response to the electromagnetic waveforms, and perform a cross correlation of the digitized returned electromagnetic wave form with at least one of the plurality of digital templates. In some embodiments, the instructions, when executed by the processor, cause the medical device identifier to perform a cross correlation of the digitized \electromagnetic wave form with each of at least two of the templates, and identify the medical device based on the template best matching the digitized returned electromagnetic waveform as determined by the cross correlations. In some embodiments, the instructions, when executed by the processor, cause the medical device identifier to, for each respective electromagnetic waveform generated, place the coil in a receive mode and digitize the output of the coil, wherein for a particular one of the generated electromagnetic waveforms the digitized output of the coil is the digitized returned electromagnetic waveform.

According to another aspect, a medical device identifier includes a housing, a printed circuit board within the housing, control electronics mounted on the printed circuit board, and a coil. The coil is positioned away from the printed circuit board and coupled to the printed circuit board for generating a sequence of electromagnetic waveforms to prompt a return signal from a medical device. The control electronics identifies the medical device based on the return signal. The coil may be coupled to the printed circuit board via a cable. The coil may be mounted in a portion that extends from the housing. In some embodiments, the control electronics further comprise a computer subsystem comprising a processor and memory, the memory holding instructions executable by the processor and holding a plurality of digital templates corresponding to different medical devices; drive circuitry coupled to the coil and the computer subsystem; and receiver circuitry coupled to the coil and the computer subsystem; wherein the instructions, when executed by the processor, cause the medical device identifier to: sequentially excite the coil via the drive circuitry to generate electromagnetic waveforms corresponding to a plurality of digitally predefined waveforms; receive and digitize via the coil and the receiver circuitry a returned electromagnetic waveform transmitted from a medical device in response to the electromagnetic waveforms; and perform a cross correlation of the digitized returned electromagnetic wave form with at least one of the plurality of digital templates. In some embodiments, the instructions, when executed by the processor, cause the medical device identifier to perform a cross correlation of the digitized electromagnetic wave form with each of at least two of the templates, and identify the medical device based on the template best matching the digitized returned electromagnetic waveform as determined by the cross correlations. In some embodiments, the control electronics further comprise a digital-to-analog converter, and the generated electromagnetic waveforms are generated in part by supplying the digitally predefined waveforms to the digital-to-analog converter.

According to another aspect, a portal device, includes a device identification subsystem configured to identify, from a plurality of possible providers, the provider of a medical device that is in proximity to the portal device; and a communication subsystem configured to establish two-way communication over an electronic link with a call center servicing medical devices from the identified provider. The portal device is operable to receive electromagnetic signals from the medical device, to forward to the call center information based on the electromagnetic signals received from the medical device, to receive communications from the call center carrying information to be transmitted to the medical device, and to transmit further electromagnetic signals to the medical device based on the communications received from the call center. In some embodiments, the portal device further includes a plurality of translation modules corresponding respectively to the plurality of possible providers. In some embodiments, each translation module is provided by its respective one of the plurality of possible providers. In some embodiments, the device identification subsystem further comprises: a coil; a computer subsystem comprising a processor and memory, the memory holding instructions executable by the processor and holding a plurality of digital templates corresponding to different medical devices; drive circuitry coupled to the coil and the computer subsystem; and receiver circuitry coupled to the coil and the computer subsystem; wherein the instructions, when executed by the processor, cause the medical device identifier to: sequentially excite the coil via the drive circuitry to generate electromagnetic waveforms corresponding to a plurality of digitally predefined waveforms; receive and digitize via the coil and the receiver circuitry a returned electromagnetic waveform transmitted from a medical device in response to the electromagnetic waveforms; and identify the provider of the medical device based on a comparison of the returned electromagnetic waveform with at least one of the plurality of digital templates. In some embodiments, the device identification subsystem further comprises a digital-to-analog converter, and wherein the generated electromagnetic waveforms are generated in part by supplying the digitally predefined waveforms to the digital-to-analog converter.

BRIEF DESCRIPTION OF THE DRAWINGS

FIG. 1 illustrates an example use of a medical device identifier according to embodiments of the invention.

FIG. 2 illustrates a coil arrangement usable in embodiments of the invention.

FIG. 3 shows a simplified block diagram of one example electronic architecture of the medical device identifier of FIG. 1.

FIGS. 4A and 4B illustrate the usage of a battery in the medical device identifier of FIG. 1.

FIG. 5 shows a hardware implementation of cross correlation.

DETAILED DESCRIPTION OF THE INVENTION

Figure 6A:
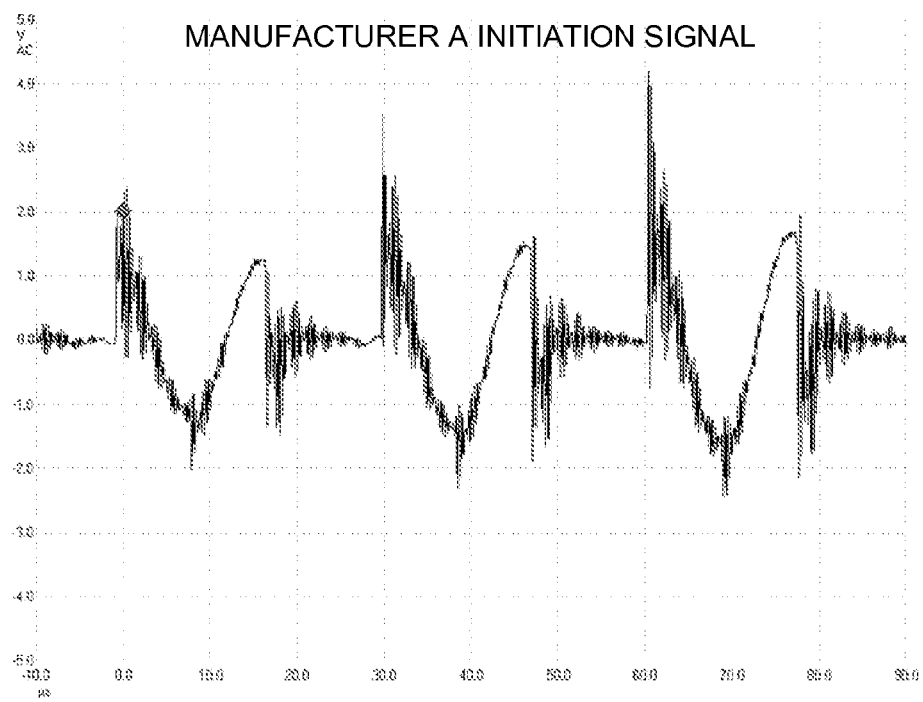
FIG. 6A illustrates a digital recording of an electromagnetic signal generated by a first manufacturer's programming device.

FIG. 1 illustrates an example use of a medical device identifier 10 according to embodiments of the invention. Medical device identifier 10 is shown close to but not necessarily touching the body of a patient 1 who has in implanted medical device 12. Implanted medical device 12 may be, for example, a pacemaker that regulates the heart 14 of patient 1. While the invention will be described primarily in the context of identifying a pacemaker, it is to be understood that the invention is not so limited, and embodiments may be used to identify other kinds of devices. A pacemaker is typically placed just under the skin. Medical device identifier 10 transmits varying or steady signals according to one or more predetermined protocols, and interprets any electromagnetic signals returned from implanted device 12 to identify the implanted device 12. Because each manufacturer uses a different protocol, the manufacturer of the device can be uniquely determined from the returned signals. For example, medical device identifier 10 may try possible manufacturers' protocols one by one until the implanted medical device responds with a returned signal. Medical device identifier 10 may then also analyze the returned signal to further verify the identification.

In some embodiments, medical device identifier 10 does not program or otherwise change the operation of implanted medical device 12, but simply gathers enough information about the device, based on the return signals, to identify the manufacturer or other provider of the device. In other embodiments, more detailed information may be ascertained, such as a model number of the device or other information. Because no programming is performed, there is no risk to the patient.

FIG. 2 illustrates a coil arrangement usable in embodiments of the invention. A primary coil 16 can be used in an active mode to generate electromagnetic signals, or in a passive mode to receive electromagnetic signals. When a current is passed through coil 16, coil 16 generates a magnetic field. If the current is time-varying, the magnetic field is also time-varying in accordance with the current waveform. In the passive mode, electromagnetic fields interacting with coil 16 generate currents within coil 16. Information about the magnetic fields can be inferred from the characteristics of the induced current. Primary coil 16 may be, for example, between 2 and 20 cm in diameter, and have between 10 and 300 turns of wire, although coils having other sizes and numbers of turns may be used in some embodiments. In one embodiment, coil 16 has a diameter of about 6.3 cm, a height of about 1.5 cm, a resistance of 0.1 ohms, and includes 16 turns of 20 gauge wire.

A secondary coil 18 may be used to generate steady (DC) magnetic fields by passing a DC current through secondary coil 18. A ferromagnetic or ferrimagnetic core 19 may be present within secondary coil 18, to enhance the strength of magnetic fields generated by secondary coil 18. Secondary coil 18 may have any suitable size, number of turns, and resistance. In one embodiment, secondary coil 18 has about 291 turns of 25 gauge wire, a diameter of about 6 cm, a height of about 1.8 cm, and a resistance of about 4.7 ohms. Other coils usable in embodiments include the Ledex Low Profile 1EC 123421-031 and the Ledex Low Profile 2EC 123422-032 available from Johnson Electric of Hong Kong, each of which has a built-in core. In some embodiments, a permanent magnet may be provided for generating DC magnetic fields.

FIG. 3 shows a simplified block diagram of one example electronic architecture of medical device identifier 10. A computer subsystem 28 includes a processor 40 and memory 42. Processor 40 may be any suitable microprocessor, microcontroller, digital signal processor, or other circuitry capable of performing the processor function. Preferably, computer subsystem 28 is capable of at least 500 kHz sampling of waveforms. An example processor usable in embodiments is the LM3S1968 microcontroller available from Texas Instruments Incorporated of Dallas, Tex., USA.

Memory 42 may include multiple kinds of memory, for example random access memory (RAM), read only memory (ROM), flash memory, and other kinds of memory, in any suitable combination. For example, memory 42 may include nonvolatile memory such as ROM or flash memory for storing instructions executed by processor 40 in performing the functions of medical device identifier 10. A number of digitized waveforms may be stored in nonvolatile memory, as is explained in more detail below. Memory 42 may include RAM used by processor 40 for temporary variable storage. While only one block is indicated for memory 42, different kinds of memory 42 may reside in different locations. For example RAM may be integrated into processor 40. Many different architectures are possible. Additional storage 46 may be provided, and may include removable storage such as a flash memory card for storing information for transfer to another computer system, allowing for diagnostics, evaluation, and improved operation.

A user interface 44 may be provided for presenting results to a user of medical device identifier 10, for accepting inputs from the user, and other functions. For example, user interface 44 may include a display such as a liquid crystal display on which results can be presented, and may also include various switches, buttons, keypads, or other input devices with which the user can direct the operation of medical device identifier 10. One example of a display usable in embodiments is an ezLCD002 display available from Earth Computer Technologies, Inc. of Costa Mesa, Calif., USA. A touchscreen could be used, providing both display and user input capabilities in a single device.

A digital-to-analog converter (DAC) 32 is coupled to processor 40 via an output port 34. DAC 32 converts digital values supplied by processor 40 to analog voltages. Any suitable DAC may be used, for example a 6-bit converter made using a simple network of resistors. The output of DAC 32 is provided to drive circuitry, which in turn is used to drive primary coil 16 in its active mode to generate electromagnetic waveforms. In the example of FIG. 3, the drive circuitry includes a voltage-to-current amplifier 30.

Coil 16 is switchable between active and passive modes by enabling and disabling amplifier 30. Processor 40 provides, via port 38, a digital signal 33 that enables and disables amplifier 30 depending on the true or false state of signal 33. When amplifier 30 is enabled, it drives current through coil 16 in accordance with the output of DAC 32. When amplifier 30 is disabled, coil 16 may be used in its passive mode.

In the passive mode, coil 16 is used to sense any electromagnetic signals returned from implanted medical device 12. As currents are induced in coil 16, a voltage appears on the leads of coil 16, corresponding to the electromagnetic signal. The leads of coil 16 are connected to receiver circuitry for reading the voltage signal. In the example of FIG. 3, the receiver circuitry includes an instrumentation amplifier 22 and filters 24. In one embodiment, instrumentation amplifier 22 is an INA111 amplifier available from Texas Instruments Incorporated, and is configured with a gain of 100.

Two different filters 24 may be provided, so that signals having different characteristics can be accommodated. For example, some implanted devices may emit electromagnetic signals that are stronger or weaker than those emitted by implanted devices from different manufacturers. The two filters may be configured with different gains, so that weak signals can be detected using a detection channel with a higher gain. In one embodiment, both filters 24 are low-pass Butterworth filters, but one of the filters is configured for unity gain, while the other is configured with a gain of 10. The two filters 24 may have different frequency cutoff characteristics as well. Thus, in combination with instrumentation amplifier 22, two reading channels are available, having gains of 100 and 1000 respectively. Filters 24 may also introduce a voltage offset, so that the expected range of voltages sensed from coil 16 does not include negative voltages after the offset is introduced. In one embodiment, an offset of 1.5 volts is used. Other embodiments may use different gains, offsets, or filter types than these examples.

The receiver circuitry may also include an analog-to-digital converter (ADC) 26. In the example of FIG. 3, the outputs of filters 24 are provided to ADC 26, which converts the voltages to digital values. Processor 40 can thus obtain a digital number representing the voltage delivered to ADC 26 by either of filters 24. It is also possible for processor 40 to sense both channels. Any suitable ADC may be used. One example of an ADC suitable for use in embodiments is a model LM3S1968 10-bit ADC available from Texas Instruments Incorporated.

A high current switch 36 is also provided, for driving secondary coil 18. Switch 36 is also controlled by processor 40 through port 38. One example of a device from which a suitable switch may be constructed is the widely-available STD12NFO6 MOSFET. Processor 40 can thus selectively cause current to pass through secondary coil 18 to generate a constant magnetic field. It is also possible to generate a DC magnetic field by driving DC current through primary coil 16.

Medical device identifier 10 may include a battery (not shown in FIG. 3), for convenient operation without being connected to mains power. In some embodiments, medical device identifier may be configured so that it will not operate while connected to the mains for safety reasons. FIG. 4A shows the system while battery 52 is being charged by a charging circuit 50. During charging mode, charging circuit 50 is plugged into an AC outlet 48 and medical device identifier 10 is off. In run mode, as shown in FIG. 4B, the electronics 54 of medical device identifier 10 are powered by battery 52, and the unit is not plugged into the AC outlet, so that medical device identifier 10 is handheld and portable.

Any suitable battery arrangement may be used. On example arrangement uses two Tenergy 31003 Lithium Li-Ion 18650 7.4V 2200 mAh battery packs to create a +7.4 V and -7.4 V supply. A third Lithium-Ion 3.7 V battery can be used to run the microcontroller in sleep mode allowing it to maintain time and date. Linear regulators produce the +5 V needed for the display and the 3.3 V needed for the microcontroller.

In operation, medical device identifier 10 generates electromagnetic signals that mimic those sent by various programmers, in an attempt to "wake up" implanted medical device 12, and monitors any signals returned from implanted medical device 12. The returned signals may be tested to see if they match signals known to be transmitted by a manufacturer's device, and the device may be identification may be based on which manufacturer's known signals match most closely with the signals returned from the device.

FIG. 6A illustrates a digital recording of an electromagnetic signal generated by a first manufacturer's (Manufacturer A) programming device when it is initiating communication with an implanted medical device from Manufacturer A. The waveform of FIG. 6A has a particular pattern and amplitude unique to Manufacturer A. Medical device identifier 10 stores a digital representation of this waveform for use in attempting to interact with devices from Manufacturer A. This digital representation may be called a digitized waveform, and is a sequence of numerical values representing the waveform amplitude at respective sample times. Other digitized waveforms are also stored, which are representations of the signals used by other manufacturers' programmers to initiate communication with their respective devices.

Figure 6B:
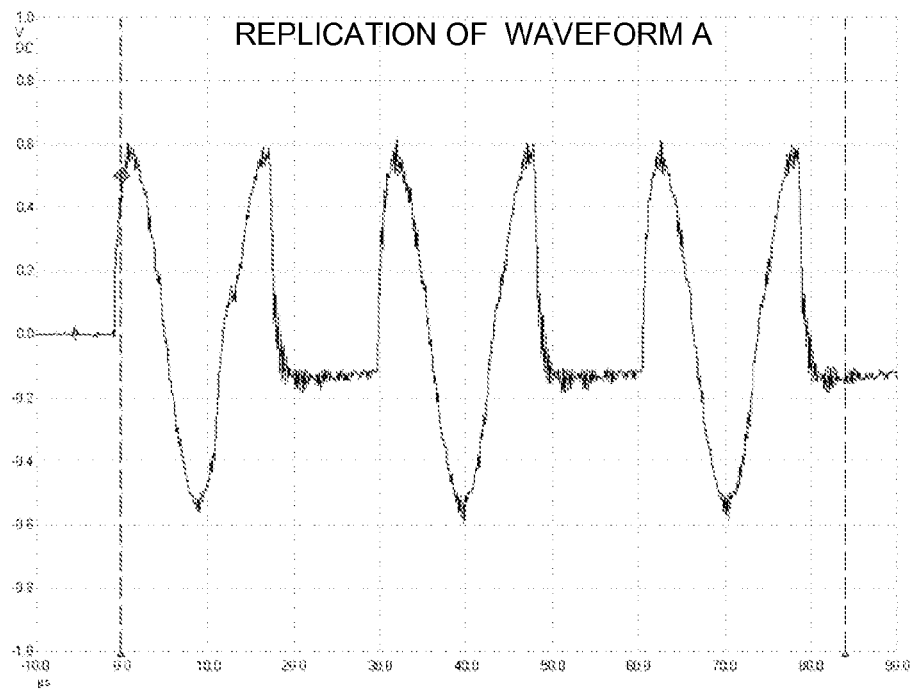
FIG. 6B is a graphical illustration of a replication of the waveform of FIG. 6A, as emitted by an embodiment of the invention.

To generate the electromagnetic signals replicating the waveform of FIG. 6A, processor 40 retrieves the corresponding digitized waveform from memory and provides the numerical values in order and with the proper timing to DAC 32, with amplifier 30 enabled so that coil 16 is in its active mode. Coil 16 thus produces electromagnetic signals very similar to those produced by the Manufacturer A's programming device. FIG. 6B shows a recording of an electromagnetic signal generated in this way by an embodiment of the invention, replicating the signal of FIG. 6A.

To receive a signal returned from implanted medical device 12, processor 40 switches coil 16 into the passive mode, and begins taking readings using the appropriate filter 24 through ADC 26. Readings are taken rapidly enough to characterize the expected signals. It is believed that any sampling rate of 350 kHz or higher is sufficient for all current pacemakers, and the data in many of the figures was taken with a sampling rate of 497.777 kHz, but any workable sampling rate may be used.

Figure 6C:
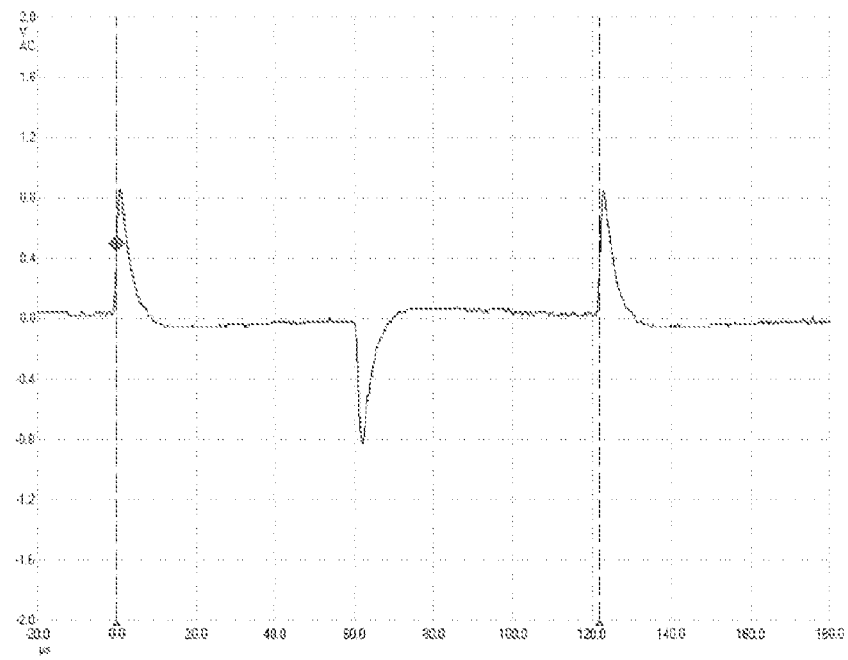
FIG. 6C illustrates a digital recording of an electromagnetic signal returned by a device made by the first manufacturer when communication is successfully initiated.
Figure 6D:
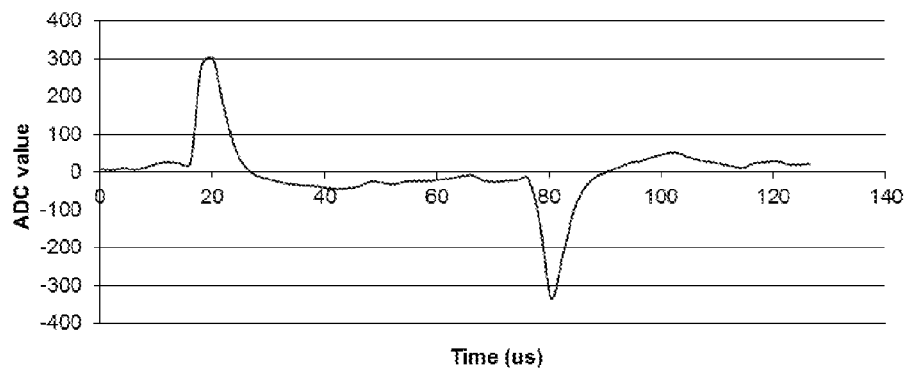
FIG. 6D is a plot of a digital template that may be used to evaluate how closely a signal returned from an implanted device matches the signal of FIG. 6C.

FIG. 6C illustrates a digital recording of an electromagnetic signal returned by a device made by Manufacturer A, when communication is successfully initiated. FIG. 6D is a plot of a digital "template" that may be used to evaluate how closely a signal returned from implanted device 12 matches the signal of FIG. 6C—that is, how well the returned signal matches a signal returned from a device made by Manufacturer A. The template is a sequence of numerical values that when plotted have the same shape as the curve of FIG. 6C. The template of FIG. 6D has 64 values, but other template sizes can be used.

In some embodiments, the comparison of the returned signal to the signal expected from a device from a particular manufacturer is made using cross correlation. The fundamental advantage of cross correlation over other methods like feature extraction is its insensitivity to noise. For continuous real variables, the cross correlation is defined as $$r_{xy}(\tau) = \lim_{T \to \infty} \frac{1}{2T} \int_{-T}^{T} x(t) y(t+\tau) dt$$

where x(t) and y(t) are two infinite-time input waveforms. If the signal x(t) is the same shape as the signal y(t) delayed by $\tau$, the $r_{xy}(\tau)$ will be high. In theory, the calculation is performed over infinite time T, but in practice a finite time is used. FIG. 5 shows a hardware implementation of the cross correlation. The signal x(t) is a known signal, called a template 56. Templates are defined in advance and stored in the machine. The signal y(t) is the observed or measured signal 58. This is the signal measured at the time of the test. The y(t) input is delayed by $\tau$=60 using a time delay function 62. A multiplier 64 creates a product, which is then integrated 66. The r($\tau$) output 60 will be +1 if the two input signals have the same shape. The $\tau$ at which the output is +1 specifies where in the y(t) signal matches the shape of the template x(t). The r($\tau$) output will be 0 if the two input signals do not have the same shape, and will be −1 if the signals have the same but inverted shapes.

Inherent in the application of cross correlation in computer based systems is the need to operate on finite sequences. Also the continuous signal x(t) is sampled at fixed time intervals x(n). In one embodiment, sampling is performed at 497.777 kHz, but the method works for any suitable sampling rate. FIG. 6D shows an example template x(n) for determining whether or not a particular medical device from Manufacturer A is communicating. The size of the templates can be varied depending on the shape medical device identifier 10 is trying to detect. It is desirable to capture a reasonable window, because the data is actually considered as an infinite periodic signal. In other words, if we process the finite sequence x(0), x(1), x(2), . . . x(N−1)

then the cross correlation will effectively be determined for the infinite sequence . . . , x(0), x(1), x(2), . . . x(N−1), x(0), x(1), x(2), . . . x(N−1), x(0), x(1), x(2), . . . x(N−1), To calculate the cross correlation on digitally-sampled data, average values are first calculated. Assume x(n) and y(n) are the sampled data, and N is the sequence length.

$$\bar{x} = \frac{1}{N} \sum_{n=0}^{n=N-1} x(n)$$

$$\bar{y} = \frac{1}{N} \sum_{n=0}^{n=N-1} y(n)$$

The discrete cross covariance is a rough measure (not scaled to any particular value) of whether or not the signals x(n) and y(n) have the same shape. The delay parameter, equivalent to the $\tau$ in the continuous case, is shown as m in the following definition of discrete cross covariance:

$$\gamma_{xy}(m) = \sum_{n=0}^{n=N-1}(x(n)-\bar{x})(y(n+m)-\bar{y})$$

The discrete cross covariance is also a finite-length sequence, but it too can be considered as an infinite periodic sequence. The cross covariance of a signal with itself at delay equal to zero is similar to its variance $$\gamma_{xy}(0) = \sum_{n=0}^{n=N-1}(x(n)-\bar{x})^2 \quad \gamma_{xy}(0) = \sum_{n=0}^{n=N-1}(y(n)-\bar{y})^2$$

The discrete cross correlation between two finite sequences x(n) and y(n) is $$r_{xy}(m) = \frac{1000 \cdot \gamma_{xy}(m)}{\sqrt{\gamma_{xx}(0)\gamma_{yy}(0)}}$$

−1,000. 7,(m)

Without the 1000 in the above equation, the correlation ranges from −1 to +1. The 1000 is included so that $r_{xy}$ will be the integer part of a fixed point number, ranging from −1000 to +1000. For example, if $r_{xy}$ is 950, it means 0.950. The higher the cross correlation value, the better the match between the template and the signal being evaluated.

The medical devices of one manufacturer communicate differently from the devices of the other manufacturers. However, there are similarities the protocols that make it possible to create medical device identifier 10. The communication begins by emitting a magnetic field into the device. Some protocols use a DC magnetic field to initiate communication, while others use a time-varying magnetic field. These protocols are very specific. For example, an attempt to communicate via the protocol of one manufacturer will typically not prompt communication from devices that are not manufactured by the same manufacturer. When an appropriate signal is received by the device, it returns another electromagnetic signal.

Figure 7A:
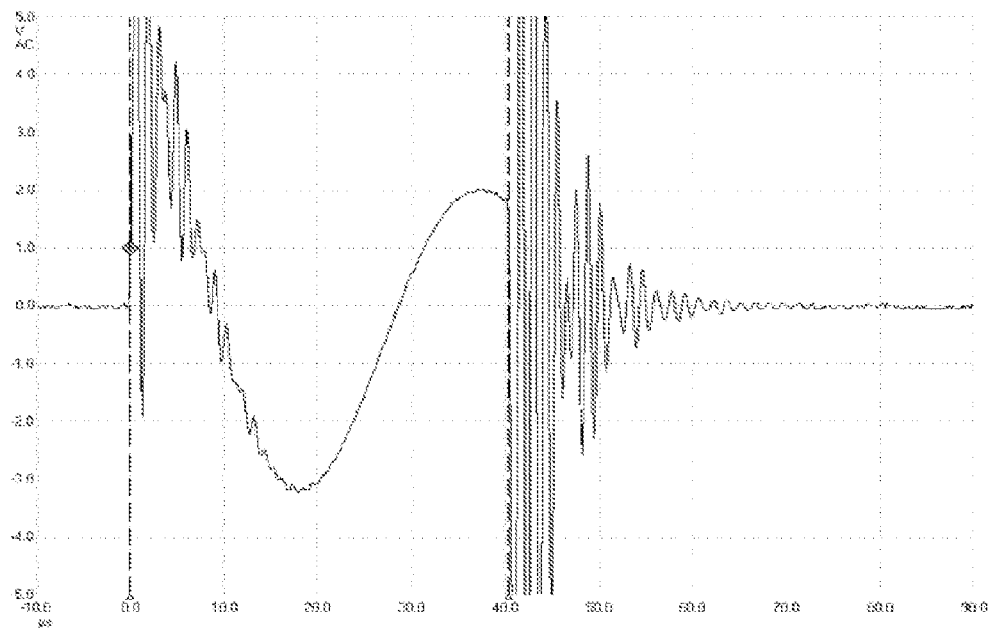
FIG. 7A illustrates a digital recording of an electromagnetic signal generated by a second manufacturer's programming device.
Figure 7B:
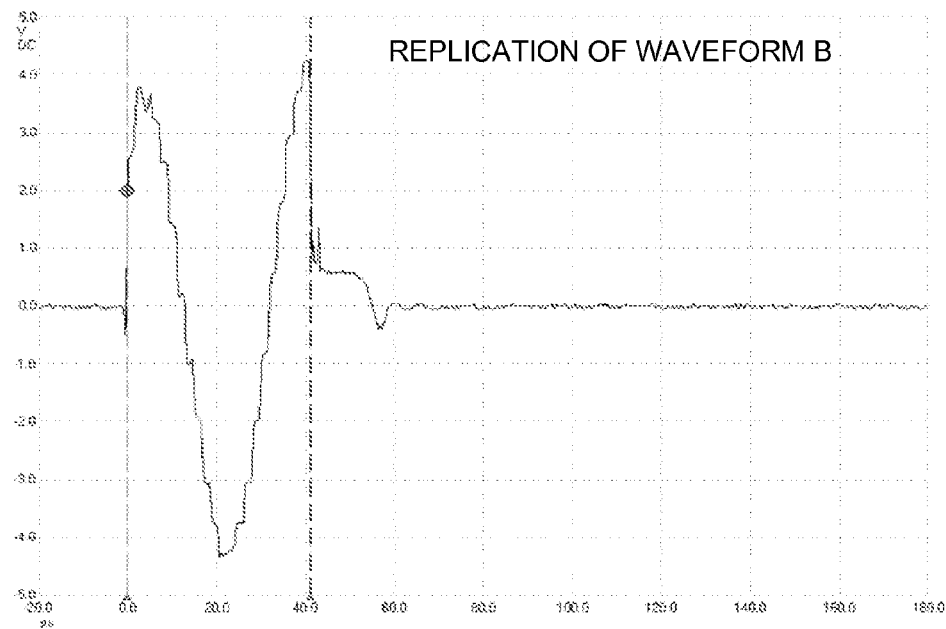
FIG. 7B is a graphical illustration of a replication of the waveform of FIG. 7A, as emitted by an embodiment of the invention.
Figure 7C:
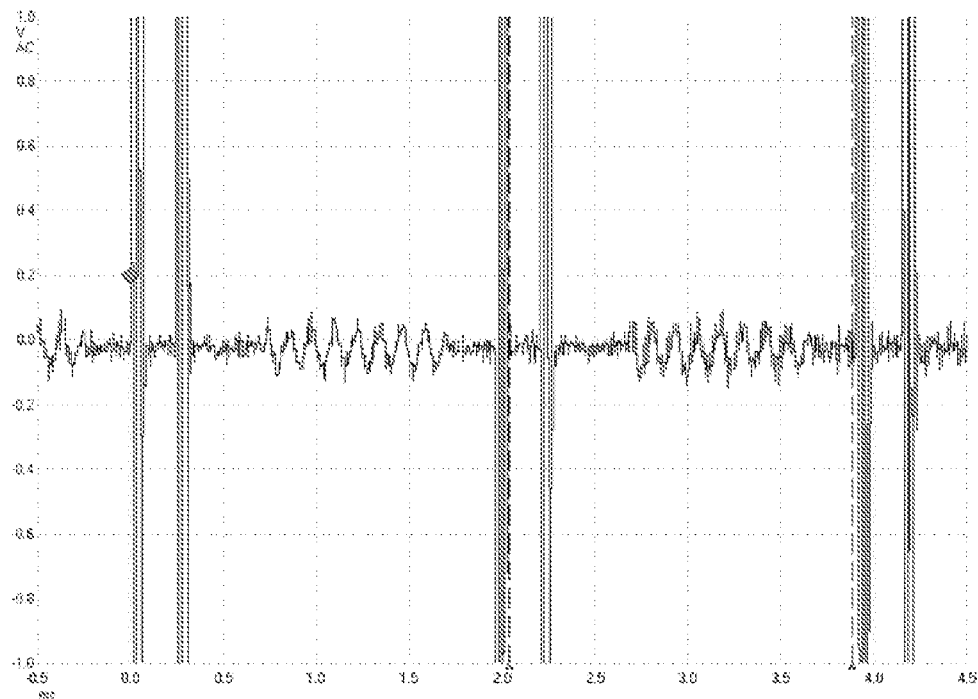
FIG. 7C illustrates a digital recording of an electromagnetic signal returned by a device made by the second manufacturer when communication is successfully initiated.
Figure 7D:
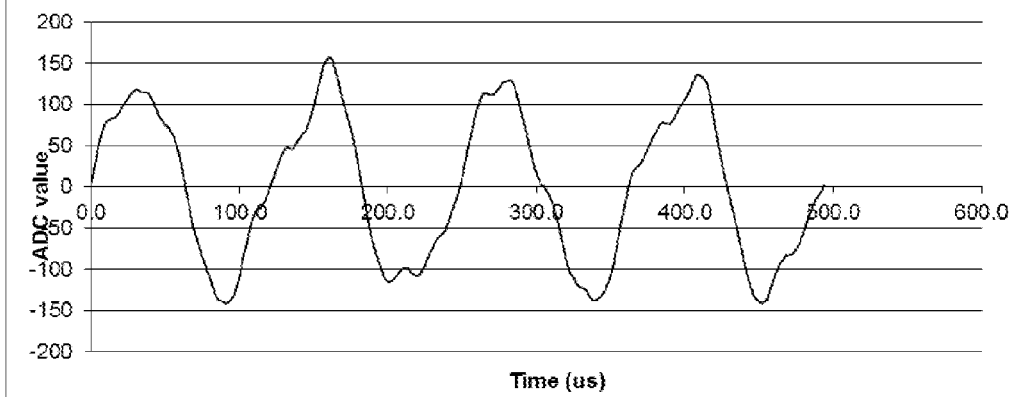
FIG. 7D is a plot of a digital template that may be used to evaluate how closely a signal returned from an implanted device matches the signal of FIG. 7C.

FIG. 7A illustrates a digital recording of an electromagnetic signal generated by a second manufacturer's (Manufacturer B) programming device when it is initiating communication with an implanted medical device from Manufacturer B. FIG. 7B shows a recording of an electromagnetic signal generated by an embodiment of the invention, replicating the signal of FIG. 7A. FIG. 7C illustrates a digital recording of an electromagnetic signal returned by a device made by Manufacturer B, when communication is successfully initiated. FIG. 7D is a plot of a digital template that may be used to evaluate how closely a signal returned from implanted device 12 matches the signal of FIG. 7C—that is, how well the returned signal matches a signal returned from a device made by Manufacturer B. The example template of FIG. 7D has 247 elements.

Figure 8A:
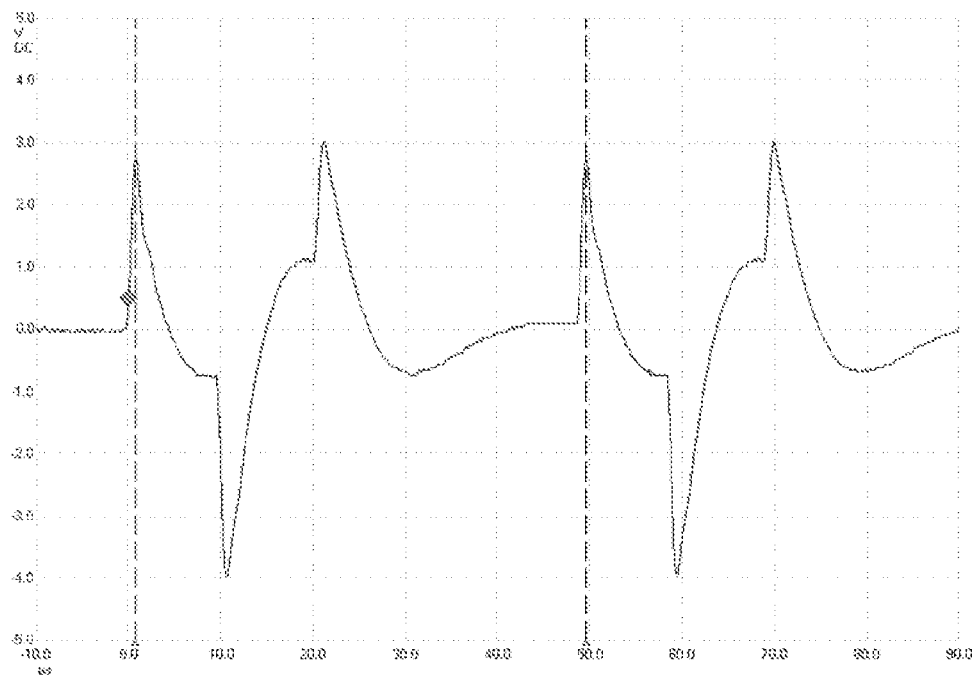
FIG. 8A illustrates a digital recording of an electromagnetic signal generated by a third manufacturer's programming device.
Figure 8B:
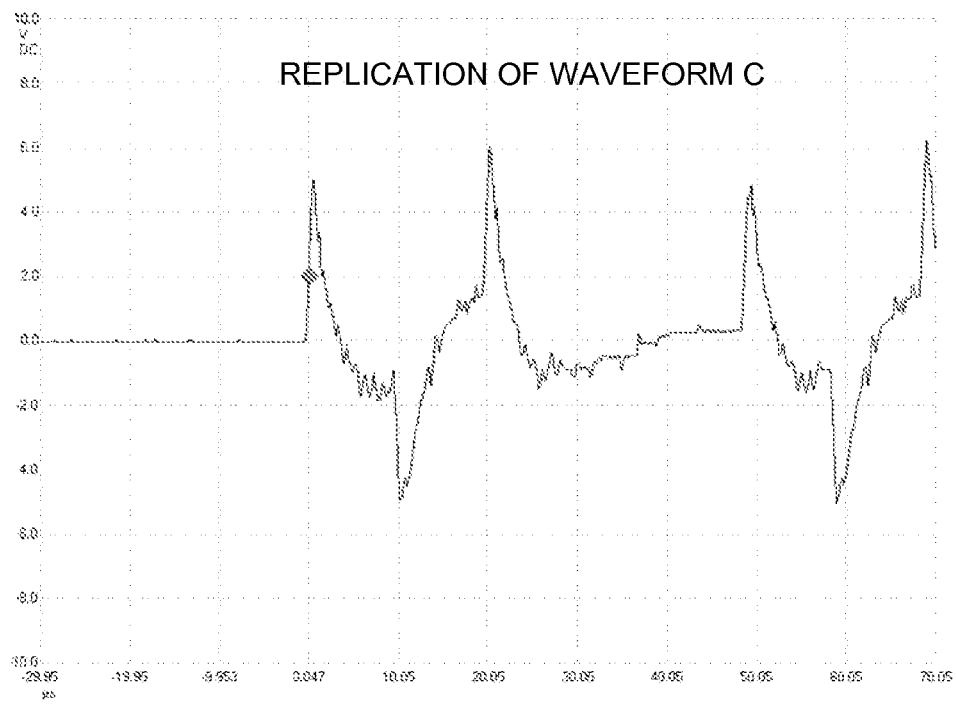
FIG. 8B is a graphical illustration of a digitization of the waveform of FIG. 8A, as emitted by an embodiment of the invention.
Figure 8C:
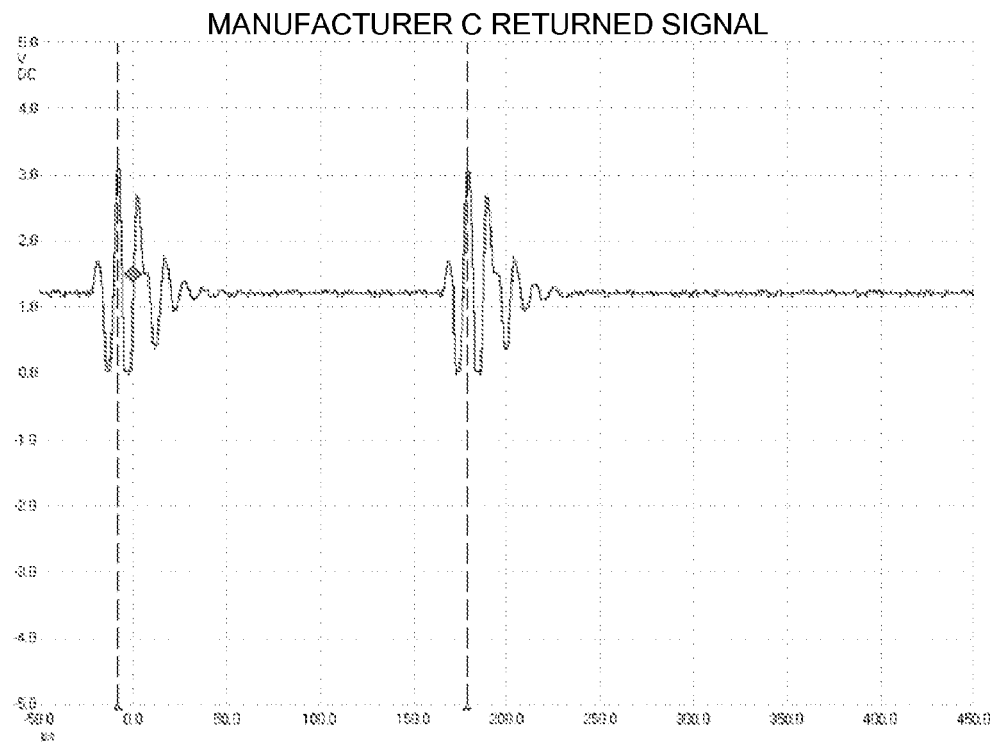
FIG. 8C illustrates a digital recording of an electromagnetic signal returned by a device made by the third manufacturer when communication is successfully initiated.
Figure 8D:
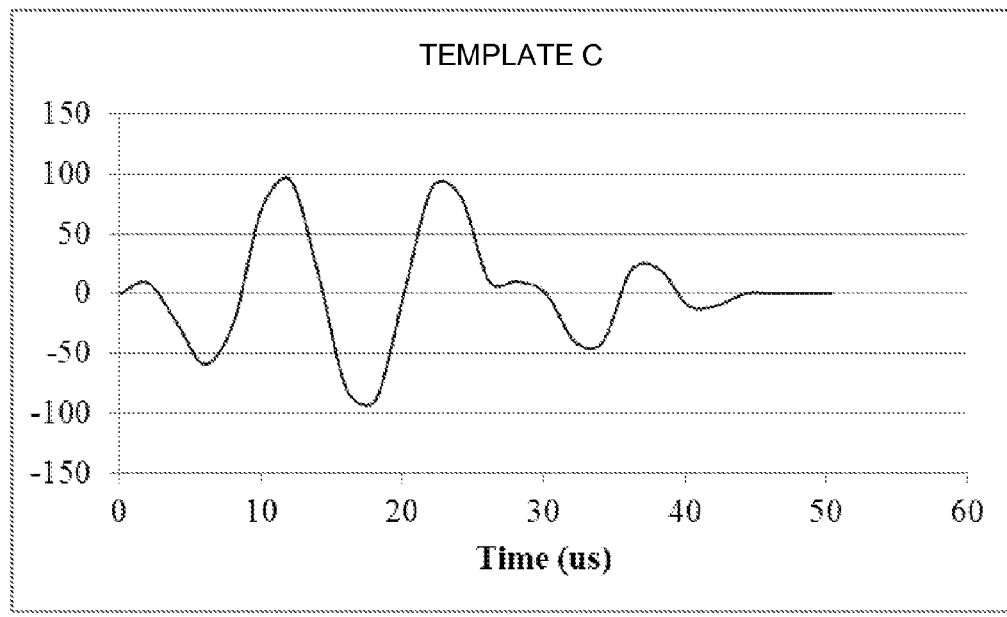
FIG. 8D is a plot of a digital template that may be used to evaluate how closely a signal returned from an implanted device matches the signal of FIG. 8C.

FIG. 8A illustrates a digital recording of an electromagnetic signal generated by a third manufacturer's (Manufacturer C) programming device when it is initiating communication with an implanted medical device from Manufacturer C. FIG. 8B shows a recording of an electromagnetic signal generated by an embodiment of the invention, replicating the signal of FIG. 8A. FIG. 8C illustrates a digital recording of an electromagnetic signal returned by a device made by Manufacturer C, when communication is successfully established. FIG. 8D is a plot of a digital template that may be used to evaluate how closely a signal returned from implanted device 12 matches the signal of FIG. 8C—that is, how well the returned signal matches a signal returned from a device made by Manufacturer C. The example template of FIG. 8D has 26 elements.

Figure 9A:
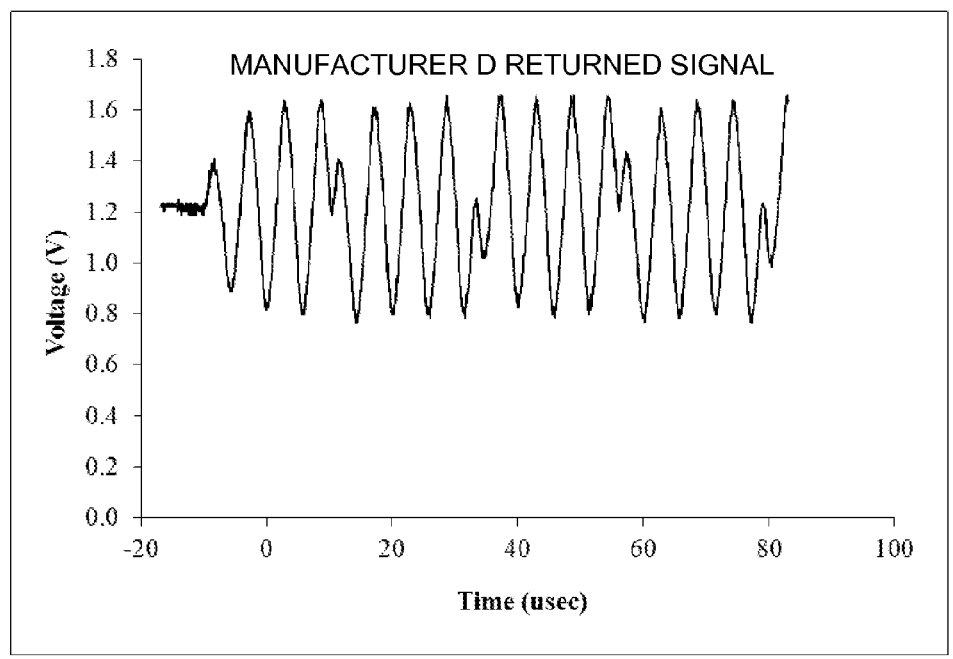
FIG. 9A shows a typical signal emitted by a pacemaker from a fourth manufacturer after communication is initiated by application of a DC magnetic field.
Figure 9B:
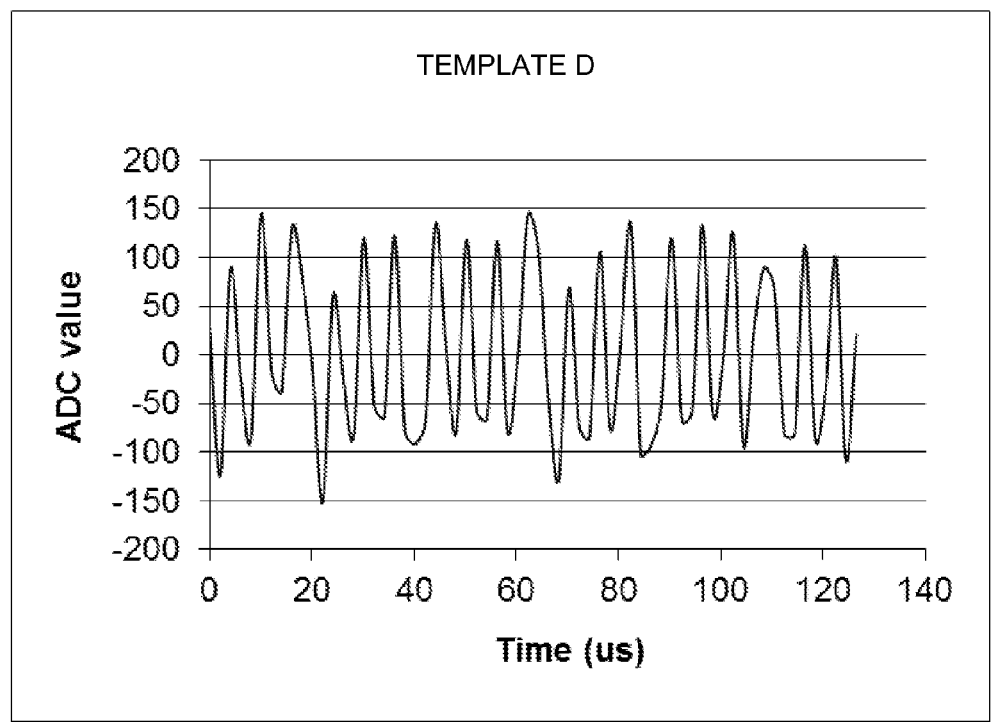
FIG. 9B is a plot of a digital template that may be used to evaluate how closely a signal returned from an implanted device matches the signal of FIG. 9A.

Devices from some manufacturers respond to simple DC magnetic fields to initiate communication. FIG. 9A shows a typical signal emitted by a pacemaker from a fourth manufacturer (Manufacturer D) after communication is initiated by application of a DC magnetic field. FIG. 9B is a plot of a digital template that may be used to evaluate how closely a signal returned from implanted device 12 matches the signal of FIG. 9A—that is, how well the returned signal matches a signal returned from a device made by Manufacturer D. The example template of FIG. 9B has 64 elements.

Figure 10A:
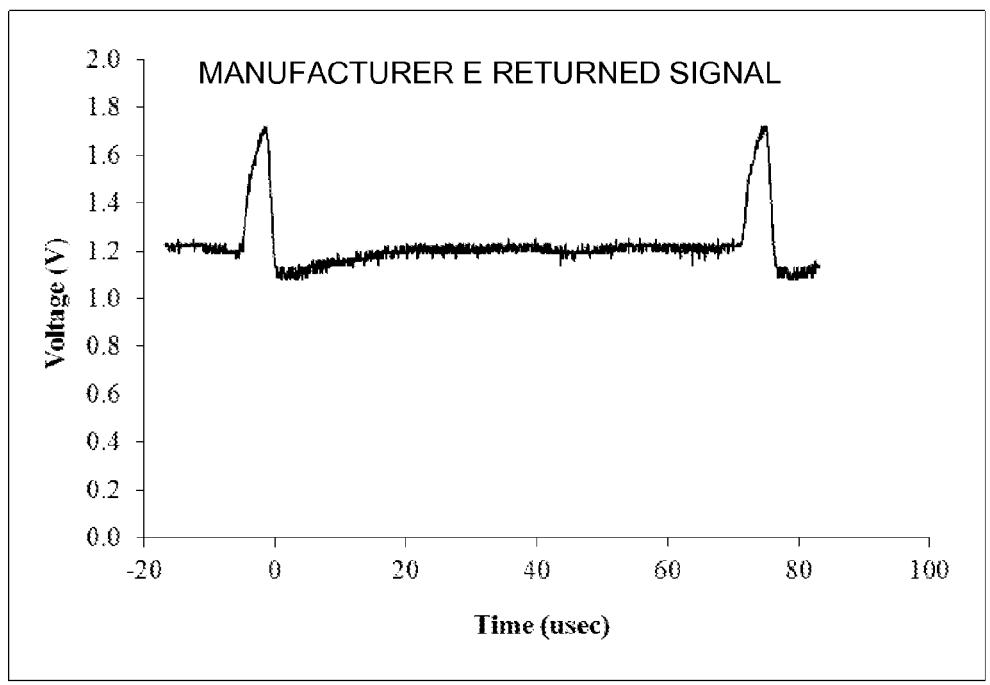
FIG. 10A shows a typical signal emitted by a pacemaker from a fifth manufacturer after communication is initiated by application of a DC magnetic field.
Figure 10B:
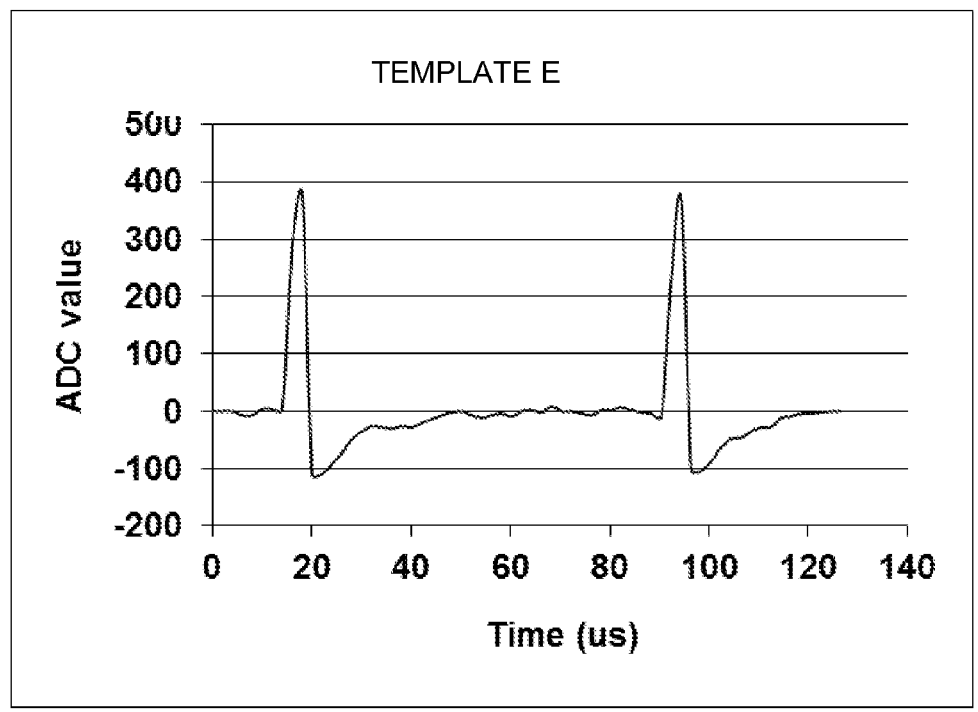
FIG. 10B is a plot of a digital template that may be used to evaluate how closely a signal returned from implanted device matches the signal of FIG. 10A.

FIG. 10A shows a typical signal emitted by a pacemaker from a fifth manufacturer (Manufacturer E) after communication is initiated by application of a DC magnetic field. FIG. 10B is a plot of a digital template that may be used to evaluate how closely a signal returned from implanted device 12 matches the signal of FIG. 10A—that is, how well the returned signal matches a signal returned from a device made by Manufacturer E. The example template of FIG. 10B has 64 elements.

While relatively short waveforms are shown in FIGS. 6A-10B, communication with various implanted devices may involve sending the appropriate signal repeatedly, with time delays between repetitions of the signal or groups of repetitions. Similarly, the device may respond with repeated transmissions of its returned waveform. These patterns can be readily determined for any particular device and manufacturer by recording the signals exchanged by the manufacturer's equipment.

Figure 11:
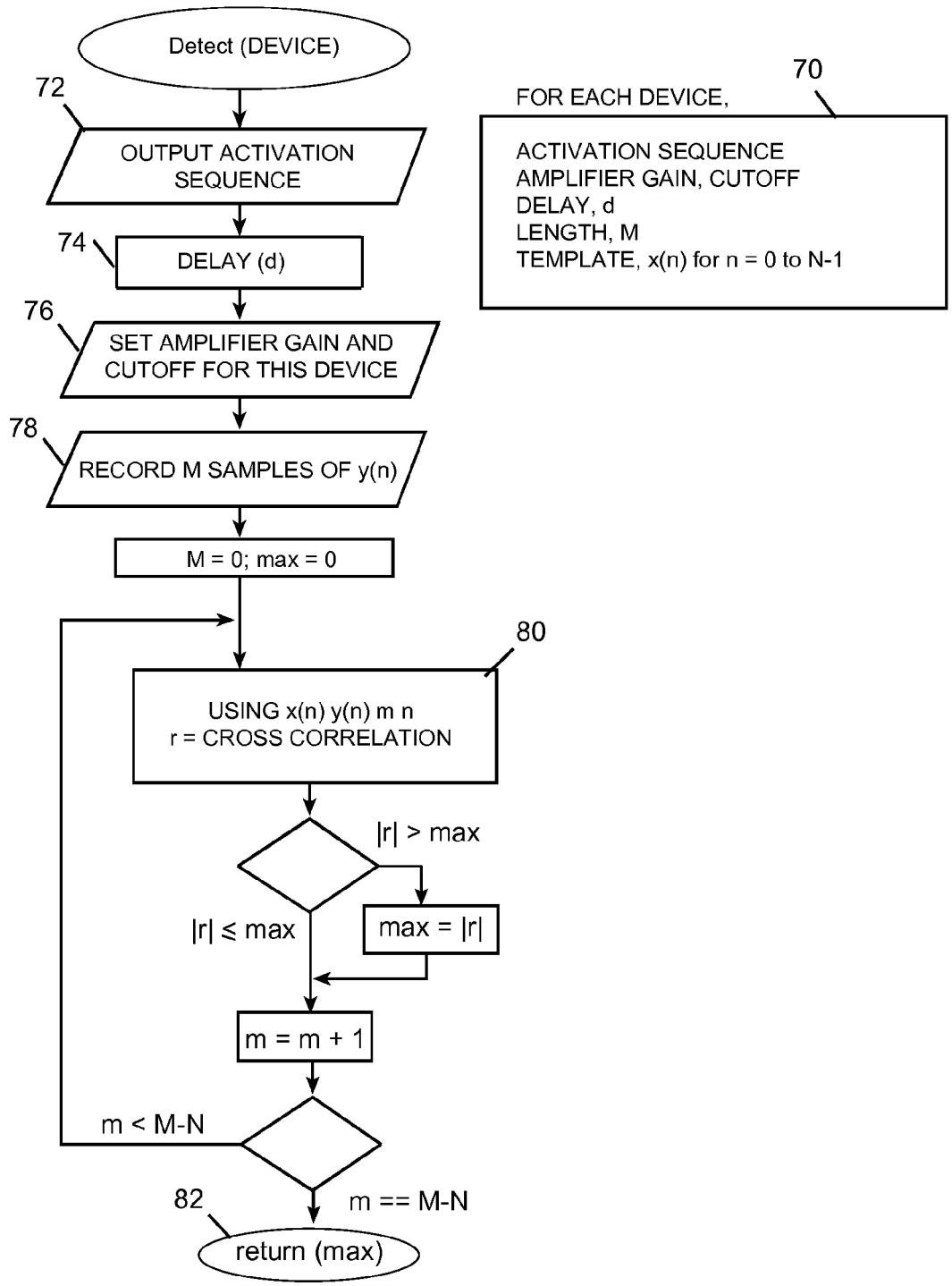
FIG. 11 is a flowchart of a method that may be used by medical device identifier to detect a medical device, in accordance with embodiments of the invention.

FIG. 11 is a flowchart of a method that may be used by medical device identifier 10 to detect a medical device, in accordance with embodiments of the invention. In this example, each device has five characteristics used for detection 70. For some devices, an activation sequence is used, in which one of the stored digitized waveforms is output to DAC 32 to initiate communication 72. FIGS. 6B, 7B, and 8B illustrate example waveforms generated by an embodiment of the invention. The activation sequence also includes the time period between DAC outputs. The sequence, the length of the sequence, and the time between outputs are unique to each manufacturer type. After sending an activation sequence, the software delays for a certain amount of time 74. This delay depends on which manufacturer type it is trying to detect. Next, the software sets the amplifier gain, cutoff, sampling rate and sample length 76. Again these sampling parameters depend on the device. The primary coil is set to passive mode and M samples are collected 78. N is the size of the template, and M will be much larger than N. For each time shift m, a cross correlation is calculated 80 as described above. Cross correlation is very robust such that broad band noise will not trigger a false detection. Cross correlation is calculated M-N times, and the largest result 82 is returned.

Figure 12:
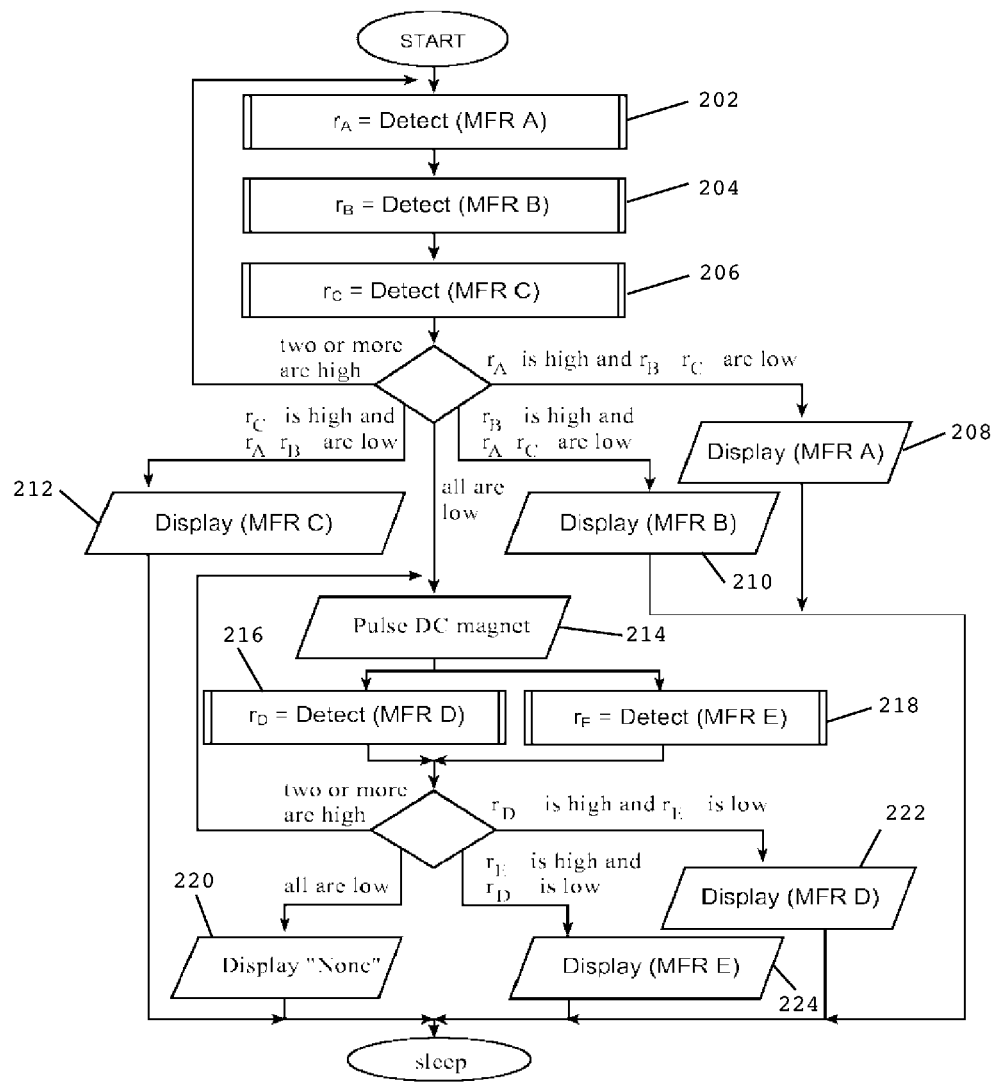
FIG. 12 is a flowchart of a method that may be used by medical device identifier to identify a medical device, in accordance with embodiments of the invention.

One by one the medical device identifier attempts to communicate with the list of potential devices as described in FIG. 12. A device is found if the detection algorithm in FIG. 11 returns a high correlation in one, and low correlations in the others. The pacemaker manufacturer may then be displayed on user interface 44 as shown in FIG. 3. Depending on the number of potential devices searched, the entire process may take only a few seconds. The devices that initiate communication upon receipt of a time-varying activation sequence are interrogated first, because the initiation process and the response are both specific to the manufacturer. Second, the DC magnetic field is applied, and all the devices that initiate communication with a DC magnetic field are searched using the same recorded ADC samples y(n).

As described in FIG. 12, a determination is made, using cross-correlation, whether returned signals from the medical device match signals known to be transmitted by a different manufacturers. At 202, a determination is made whether the device is manufactured by manufacturer A is determined. At 204, a determination is made whether the device is manufactured by manufacturer B. At 206, a determination is made whether the device is manufactured by manufacturer C. If the determination results in the identity of two or more devices being returned, the determination can be repeated.

At 208, manufacturer A will be displayed on a display device in response to determining that the cross-correlation revealed the medical device to be manufactured by manufacturer A. At 210, manufacturer B will be displayed on a display device in response to determining that the cross-correlation revealed the medical device to be manufactured by manufacturer B. At 212, manufacturer C will be displayed on a display device in response to determining that the cross-correlation revealed the medical device to be manufactured by manufacturer C.

At 214, in response to the cross-correlation indicating that no manufacturer of the medical device has been identified, a DC magnet can be pulsed. All the devices that initiate communication with a DC magnetic field are searched using the same recorded ADC samples y(n). At 216, a determination can be made as to whether manufacture D manufactured the medical device. At 218, a determination can be made as to whether manufacture E manufactured the medical device. If the determination indicates more than one manufacture, the DC magnet can be pulsed again and the determination can be redone.

At 220, if no determination can be made as to the manufacturer of the medical device, "None" can be displayed. At 222, in response to determining that manufacture D manufactured the medical device, manufacture D can be displayed. At 224, in response to determining that manufacture E manufactured the medical device, manufacture E can be displayed.

It will be recognized that medical device identifier 10 need not interpret or recognize any content in the signal being received from a medical device in order to identify the device. Medical device identifier need only associate some unique feature of the returned signal with a particular device manufacturer.

Many variations and optional features are possible. For example, measured responses and calculated correlation coefficients can be recorded in storage 46, as shown in FIG. 3. Possibilities for this storage include but are not limited to internal flash EEPROM of the microcontroller or an external secure digital card (SDC). The time and date can be entered when the batteries are installed into medical device identifier 10. In sleep mode, the medical device identifier 10 may maintain the time and date. Medical personal can retrieve this data along with time and date, and this data can be used to improve the accuracy of the device.

In some embodiments, rather than requiring one correlation to be high and the remaining correlations low, the MDI could simply report the device with the highest correlation.

For each particular region of the world, probabilities may be known a priori of finding the devices of each manufacturer. These a priori expectations could be used as weighting factors when the medical device identifier is choosing between two or more potential matches.

A medical device identifier according to embodiments may be easily adaptable to future medical devices that use magnetic fields to communicate. To identify a new device, the medical device identifier would be supplied with a digitized waveform of the magnetic field needed to initiate communication, and with programming to detect aspects of any returned signal, for example the signal shape, amplitude, or frequency components. Other than a simple software upgrade, additional devices can be added without major design changes.

In other embodiments, a medical device identifier may identify medical devices that use means other than magnetic fields to communicate. For example, future medical devices may communicate using channels such as RF radio, ZigBee®, Texas Instruments SimpliciTI®, Bluetooth®, and IEEE 802.11®. A medical device identifier would include circuitry for communicating on the channel used by the medical devices to be identified, and would be provided with any field generation information needed to initiate communication. The responses from the device to be identified would be analyzed, and an identification made based on the results.

While cross correlation has certain advantages as a method of recognizing a returned waveform, a number of methods are possible for determining whether or not a certain event has occurred. The medical device identifier could perform a discrete Fourier Transform (DFT) and look for specific frequencies emitted by the device. For example, the fundamental frequency emitted by Manufacturer D pacemakers is 175 kHz. Frequencies used by other devices are listed in Table 1.

TABLE 1

Carrier frequencies used by the major pacemaker companies

| Pacemaker | Frequency |
| --- | --- |
| Manufacturer D | 175 kHz |
| Manufacturer C | 82 kHz |
| Manufacturer A | 64 kHz |
| Manufacturer B | 58 kHz |

Another method to determine whether or not an event has occurred is feature extraction. Features include but are not limited to time between pulses, the width of a pulse, the area of a pulse, the energy of a pulse, and the direction of a pulse. Another feature existing in these waves is phase shifts and the time between phase shifts.

In some embodiments, a medical device identifier may be attached to or built into an existing pacemaker programmer to determine if the programmer is being used on the correct pacemaker. If not correct, our device could alert the operator which programmer should be used.

Figure 13:
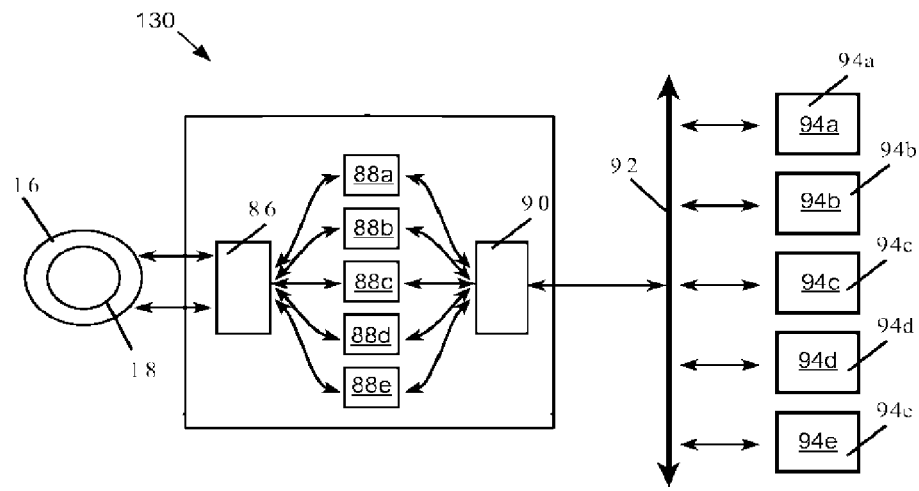
FIG. 13 shows a simplified block diagram of a portal device in accordance with embodiments of the invention.

In another aspect, a medical device identifier such as medical device identifier 10 may be a component of a universal programmer or portal device. FIG. 13 shows a simplified block diagram of a portal device 130 in accordance with embodiments of the invention.

In the system of FIG. 13, the block 86 is part of an identification subsystem that is configured to identify, from a plurality of possible providers, the provider of a medical device that is in proximity to portal device 130. For the purposes of this disclosure, for a device to be "configured" to accomplish a result or perform a step or function means that the device includes an arrangement of hardware, programming, or both, that causes the result to occur or the step or function to be performed. The identification subsystem may operate in any workable manner, for example as described above with respect to the system of FIG. 3. In such an embodiment, portal device 130 may emit an electromagnetic signal using coil 16, and receive a returned electromagnetic signal from the medical device to be identified via coil 18. The returned electromagnetic signal may be digitized, and the portal device may then identify the medical device manufacturer or other provider based on the digitized returned waveform.

Portal device 130 also includes a communications subsystem 90, through which portal device 130 can establish two-way communication over an electronic link 92 with any of a plurality of call centers 94a-94e. Call centers 94a-94e are operated by respective medical device providers, for example Manufacturers A-E as discussed above. Electronic link 92 may be any suitable communication channel, for example a telephone or Internet channel, and may utilize any workable protocol, such as but not limited to TCP/IP.

Once the identification subsystem has identified the provider of the medical device, it establishes communication over link 92 with the corresponding provider's call center. Portal device 130 can then act as a relay device, relaying information received from the medical device to the appropriate call center, and relaying information from the call center to the medical device. For example, portal device 130 may include a number of translation modules 88a-88e, for interpreting electromagnetic signals received from the medical device and converting them to information to be transmitted to the appropriate call center, and for converting information received from the call center to an appropriate digital waveform to be transmitted to the medical device. Translation modules 88a-88e may be, for example, software or firmware libraries provided by the medical device manufacturers, to be executed by a processor within portal device 130. In this way, the maker of portal device 130 does not need to know the meanings of waveforms exchanged with the medical device. Rather, portal device 130 may merely blindly convert and forward information from the appropriate call center to the medical device and waveforms received from the medical device to the appropriate call center, without knowledge of the communication protocols used by the various medical device providers. Personnel at the appropriate call center can then interact directly with the implanted device, reading information from it, or in cooperation with the attending physician may even reprogram the device from their remote location. This arrangement may eliminate the need for a medical device manufacturer to provide a network of service personnel, and may enable manufacturers to enter markets that have been previously uneconomical.

Figure 14A:
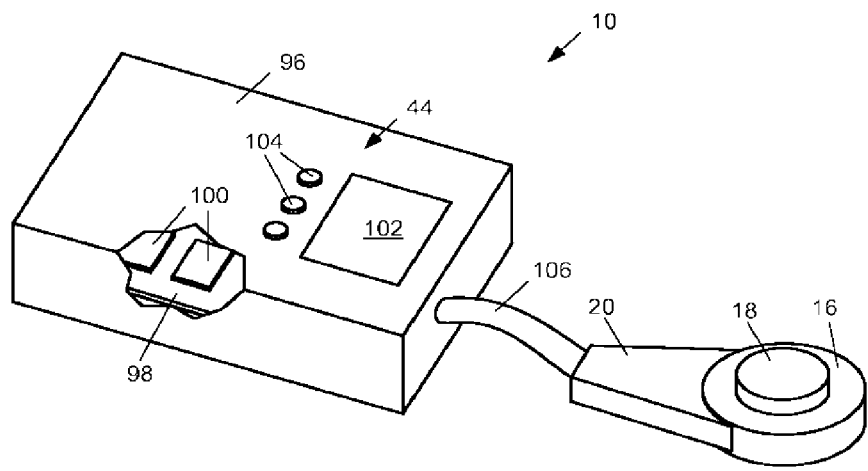
FIGS. 14A and 14B illustrate example mechanical architectures for a medical device identifier.
Figure 14B:
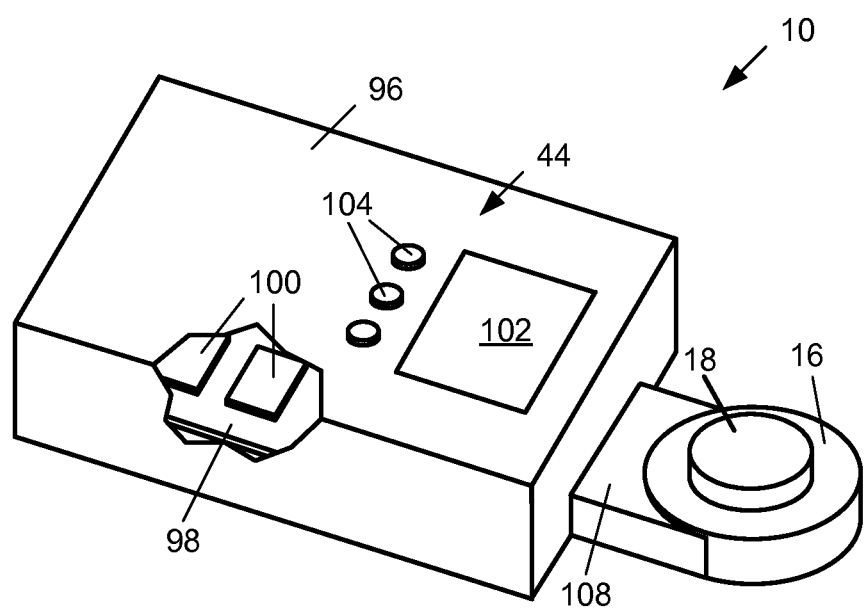

FIGS. 14A and 14B illustrates example mechanical architectures for a medical device identifier 10. In the embodiment of FIG. 14A, example medical device identifier 10 includes a housing 96 and a printed circuit board 98 within housing 96 carrying control electronics 100. Control electronics 100 may implement a circuit like that shown schematically in FIG. 3. User interface 44 includes a display 102 and various buttons or other input devices 104. Coils 16 and 18 are positioned away from printed circuit board 98, so as to avoid interference with the operation of coils 16 and 18. Coils 16 and 18 may be conveniently mounted to a handle 20, and coupled to printed circuit board 98 via a cable 106. In the embodiment of FIG. 14B, coils 16 and 18 are mounted in portion 108 that extends from housing 96.

Figure 15:
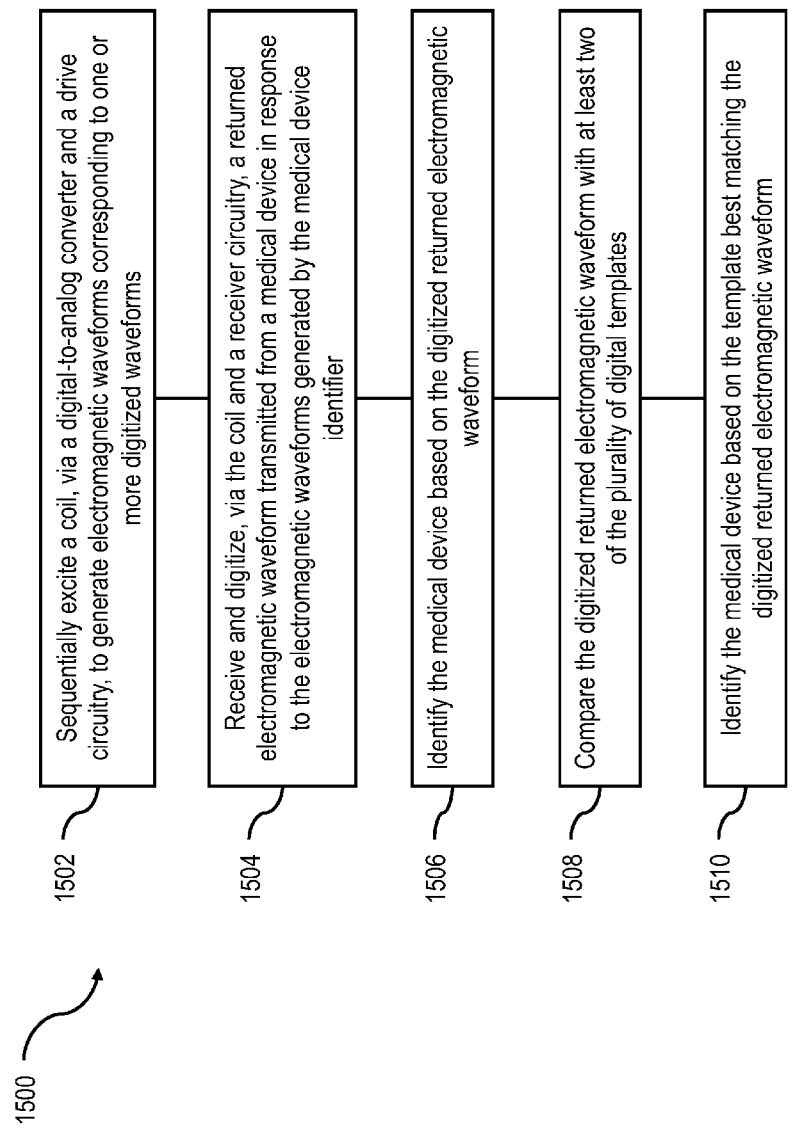
FIG. 15 illustrates a process flow diagram having one or more features consistent with the present description.

FIG. 15 is a process flow diagram 1500 having one or more features consistent with the present description. The operations described in process flow diagram 1500 can be performed by one or more devices. In some variations, individual operations may be split into two or more operations. Similarly, multiple operations may be combined into a single At 1502, a coil can be sequentially excited. Sequential excitement can occur via a digital-to-analog converter and a drive circuitry, to generate electromagnetic waveforms corresponding to one or more digitized waveforms At 1504, a returned electromagnetic waveform transmitted from a medical device can be received and digitized via the coil and a receiver circuitry. The electromagnetic waveform can be transmitted from the medical device in response to the electromagnetic waveforms generated by the medical device identifier At 1506, the medical device can be identified based on the digitized returned electromagnetic waveform At 1508, the digitized returned electromagnetic waveform can be compared with at least two of the plurality of digital templates.

At 1510, the medical device can be identified based on the template best matching the digitized returned electromagnetic waveform.

Figure 16:
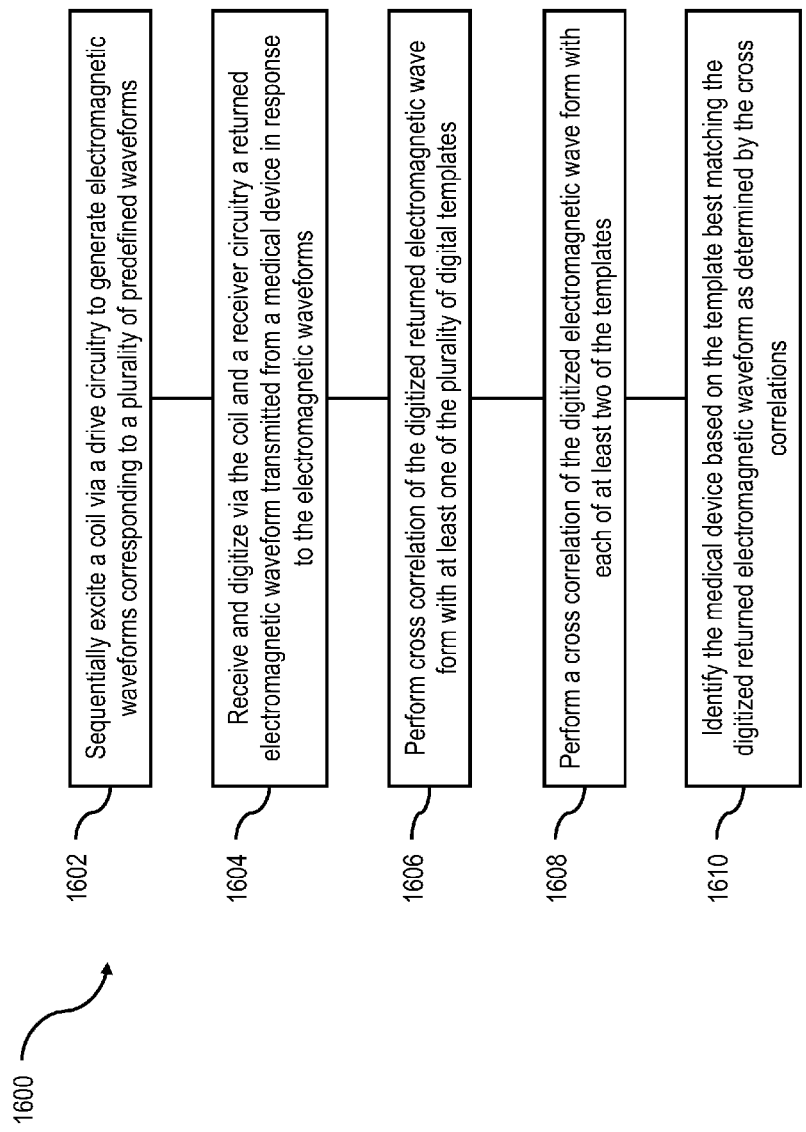
FIG. 16 illustrates a process flow diagram having one or more features consistent with the present description.

FIG. 16 is a process flow diagram 1600 having one or more features consistent with the present description. The operations described in process flow diagram 1600 can be performed by one or more devices. In some variations, individual operations may be split into two or more operations. Similarly, multiple operations may be combined into a single At 1602, a coil can be sequentially excited via a drive circuitry to generate electromagnetic waveforms corresponding to a plurality of predefined waveforms.

At 1604, a returned electromagnetic waveform transmitted from a medical device can be received and digitized via the coil and a receiver circuitry in response to the electromagnetic waveforms.

At 1606, cross correlation of the digitized returned electromagnetic wave form can be cross correlated with at least one of the plurality of digital templates At 1608, a cross correlation can be performed of the digitized electromagnetic wave form with each of at least two of the templates At 1610, the medical device can be identified based on the template best matching the digitized returned electromagnetic waveform as determined by the cross correlations.

Embodiments of the invention have now been described in detail for the purposes of clarity and understanding. However, those skilled in the art will appreciate that certain changes and modifications may be practiced within the scope of the appended claims. It is to be understood that all workable combinations of the features and elements disclosed herein are also considered to be disclosed.

EMBODIMENTS

Embodiment 1

A medical device identifier, comprising: a coil; a computer subsystem comprising a processor and memory, the memory holding instructions executable by the processor and also holding a plurality of digitized waveforms; a digital-to-analog converter coupled to the processor; drive circuitry coupled to the coil and the digital-to-analog converter; and receiver circuitry coupled to the coil and the computer subsystem; wherein the instructions, when executed by the processor, cause the medical device identifier to: sequentially excite the coil, via the digital-to-analog converter and the drive circuitry, to generate electromagnetic waveforms corresponding to one or more of the digitized waveforms; receive and digitize, via the coil and the receiver circuitry, a returned electromagnetic waveform transmitted from a medical device in response to the electromagnetic waveforms generated by the medical device identifier; and identify the medical device based on the digitized returned electromagnetic waveform.

Embodiment 2

The medical device identifier of embodiment 1, wherein the memory further holds a plurality of digital templates corresponding to different medical devices, and wherein the instructions, when executed by the processor, cause the medical device identifier to identify the medical device based on a comparison of the digitized returned electromagnetic waveform with the plurality of digital templates.

Embodiment 3

The medical device identifier of any one of the embodiments 1 and 2, wherein the comparison of the digitized returned electromagnetic waveform with a respective one of the digital templates comprises a cross-correlation of the digitized returned electromagnetic waveform with the respective digital template.

Embodiment 4

The medical device identifier of any one of the embodiments 1-3, wherein the instructions, when executed by the processor, cause the medical device identifier to: compare the digitized returned electromagnetic waveform with at least two of the plurality of digital templates; and identify the medical device based on the template best matching the digitized returned electromagnetic waveform.

Embodiment 5

The medical device identifier of any one of the embodiments 1-4, wherein the medical device identifier further produces a constant magnetic field to attempt to prompt a response from the medical device.

Embodiment 6

The medical device identifier of any one of the embodiments 1-5, wherein the instructions, when executed by the processor, cause the medical device identifier to, for each respective electromagnetic waveform generated, place the coil in a receive mode and digitize the output of the coil, wherein for a particular one of the generated electromagnetic waveforms the digitized output of the coil is the digitized returned electromagnetic waveform.

Embodiment 7

A medical device identifier, comprising: a coil; a computer subsystem comprising a processor and memory, the memory holding instructions executable by the processor and holding a plurality of digital templates corresponding to different medical devices; drive circuitry coupled to the coil and the computer subsystem; and receiver circuitry coupled to the coil and the computer subsystem; wherein the instructions, when executed by the processor, cause the medical device identifier to: sequentially excite the coil via the drive circuitry to generate electromagnetic waveforms corresponding to a plurality of digitally predefined waveforms; receive and digitize via the coil and the receiver circuitry a returned electromagnetic waveform transmitted from a medical device in response to the electromagnetic waveforms; and perform a cross correlation of the digitized returned electromagnetic wave form with at least one of the plurality of digital templates.

Embodiment 8

The medical device identifier of embodiment 7, wherein the instructions, when executed by the processor, cause the medical device identifier to: perform a cross correlation of the digitized electromagnetic wave form with each of at least two of the templates; and identify the medical device based on the template best matching the digitized returned electromagnetic waveform as determined by the cross correlations.

Embodiment 9

The medical device identifier of any one of the embodiments 7 and 8, wherein the instructions, when executed by the processor, cause the medical device identifier to, for each respective electromagnetic waveform generated, place the coil in a receive mode and digitize the output of the coil, wherein for a particular one of the generated electromagnetic waveforms the digitized output of the coil is the digitized returned electromagnetic waveform.

Embodiment 10

A medical device identifier, comprising: a housing; a printed circuit board within the housing; control electronics mounted on the printed circuit board; and a coil positioned away from the printed circuit board and coupled to the printed circuit board for generating a sequence of electromagnetic waveforms to prompt a return signal from a medical device; wherein the control electronics identifies the medical device based on the return signal.

Embodiment 11

The medical device identifier of embodiment 10, wherein the coil is coupled to the printed circuit board via a cable.

Embodiment 12

The medical device identifier of embodiment 10, wherein the coil is mounted in a portion that extends from the housing.

Embodiment 13

The medical device identifier of any of the embodiments 10-12, wherein the control electronics further comprise: a computer subsystem comprising a processor and memory, the memory holding instructions executable by the processor and holding a plurality of digital templates corresponding to different medical devices; drive circuitry coupled to the coil and the computer subsystem; and receiver circuitry coupled to the coil and the computer subsystem; wherein the instructions, when executed by the processor, cause the medical device identifier to: sequentially excite the coil via the drive circuitry to generate electromagnetic waveforms corresponding to a plurality of digitally predefined waveforms; receive and digitize via the coil and the receiver circuitry a returned electromagnetic waveform transmitted from a medical device in response to the electromagnetic waveforms; and perform a cross correlation of the digitized returned electromagnetic wave form with at least one of the plurality of digital templates.

Embodiment 14

The medical device identifier of any of the embodiments 10-13, wherein the instructions, when executed by the processor, cause the medical device identifier to: perform a cross correlation of the digitized electromagnetic wave form with each of at least two of the templates; and identify the medical device based on the template best matching the digitized returned electromagnetic waveform as determined by the cross correlations.

Embodiment 15

The medical device identifier of any of the embodiments 10-14, wherein the control electronics further comprise a digital-to-analog converter, and wherein the generated electromagnetic waveforms are generated in part by supplying the digitally predefined waveforms to the digital-to-analog converter.

Embodiment 16

A portal device, comprising: a device identification subsystem configured to identify, from a plurality of possible providers, the provider of a medical device that is in proximity to the portal device; and a communication subsystem configured to establish two-way communication over an electronic link with a call center servicing medical devices from the identified provider; wherein the portal device is operable to receive electromagnetic signals from the medical device, to forward to the call center information based on the electromagnetic signals received from the medical device, to receive communications from the call center carrying information to be transmitted to the medical device, and to transmit further electromagnetic signals to the medical device based on the communications received from the call center.

Embodiment 17

The portal device of embodiment 16, further comprising a plurality of translation modules corresponding respectively to the plurality of possible providers.

Embodiment 18

The portal device of embodiment 17, wherein each translation module is provided by its respective one of the plurality of possible providers.

Embodiment 19

The portal device of any of the embodiments 16-18, wherein the device identification subsystem further comprises: a coil; a computer subsystem comprising a processor and memory, the memory holding instructions executable by the processor and holding a plurality of digital templates corresponding to different medical devices; drive circuitry coupled to the coil and the computer subsystem; and receiver circuitry coupled to the coil and the computer subsystem; wherein the instructions, when executed by the processor, cause the medical device identifier to: sequentially excite the coil via the drive circuitry to generate electromagnetic waveforms corresponding to a plurality of digitally predefined waveforms; receive and digitize via the coil and the receiver circuitry a returned electromagnetic waveform transmitted from a medical device in response to the electromagnetic waveforms; and identify the provider of the medical device based on a comparison of the returned electromagnetic waveform with at least one of the plurality of digital templates.

Embodiment 20

The portal device of any of the embodiments 16-19, wherein the device identification subsystem further comprises a digital-to-analog converter, and wherein the generated electromagnetic waveforms are generated in part by supplying the digitally predefined waveforms to the digital-to-analog converter.

What is claimed is:

1. A medical device identifier, comprising:
   a coil;
   a computer subsystem comprising a processor and memory, the memory holding instructions executable by the processor and also holding a plurality of digitized waveforms;
   a digital-to-analog converter coupled to the processor;
   drive circuitry coupled to the coil and the digital-to-analog converter; and
   receiver circuitry coupled to the coil and the computer subsystem;
   wherein the instructions, when executed by the processor, cause the medical device identifier to:
   sequentially excite the coil, via the digital-to-analog converter and the drive circuitry, to generate electromagnetic waveforms corresponding to one or more of the digitized waveforms;
   receive and digitize, via the coil and the receiver circuitry, a returned electromagnetic waveform transmitted from a medical device in response to the electromagnetic waveforms generated by the medical device identifier; and
   identify the medical device based on the digitized returned electromagnetic waveform, wherein the memory further holds a plurality of digital templates corresponding to different medical devices, and wherein the instructions, when executed by the processor, cause the medical device identifier to identify the medical device based on a comparison of the digitized returned electromagnetic waveform with the plurality of digital templates.

2. The medical device identifier of claim 1, wherein the comparison of the digitized returned electromagnetic waveform with a respective one of the digital templates comprises a cross-correlation of the digitized returned electromagnetic waveform with the respective digital template.

3. The medical device identifier of claim 1, wherein the instructions, when executed by the processor, cause the medical device identifier to, for each respective electromagnetic waveform generated, place the coil in a receive mode and digitize the output of the coil, wherein for a particular one of the generated electromagnetic waveforms the digitized output of the coil is the digitized returned electromagnetic waveform.

4. The medical device identifier of claim 1, wherein the instructions, when executed by the processor, cause the medical device identifier to:
   compare the digitized returned electromagnetic waveform with at least two of the plurality of digital templates; and
   identify the medical device based on the template best matching the digitized returned electromagnetic waveform.

5. The medical device identifier of claim 4, wherein the medical device identifier further produces a constant magnetic field to attempt to prompt a response from the medical device.

6. A medical device identifier, comprising:
   a coil;
   a computer subsystem comprising a processor and memory, the memory holding instructions executable by the processor and holding a plurality of digital templates corresponding to different medical devices;
   drive circuitry coupled to the coil and the computer subsystem; and
   receiver circuitry coupled to the coil and the computer subsystem;
   wherein the instructions, when executed by the processor, cause the medical device identifier to:
   sequentially excite the coil via the drive circuitry to generate electromagnetic waveforms corresponding to a plurality of digitally predefined waveforms;
   receive and digitize via the coil and the receiver circuitry a returned electromagnetic waveform transmitted from a medical device in response to the electromagnetic waveforms; and
   perform a cross correlation of the digitized returned electromagnetic wave form with at least one of the plurality of digital templates.

7. The medical device identifier of claim 6, wherein the instructions, when executed by the processor, cause the medical device identifier to:
   perform a cross correlation of the digitized electromagnetic wave form with each of at least two of the templates; and
   identify the medical device based on the template best matching the digitized returned electromagnetic waveform as determined by the cross correlations.

8. The medical device identifier of claim 6, wherein the instructions, when executed by the processor, cause the medical device identifier to, for each respective electromagnetic waveform generated, place the coil in a receive mode and digitize the output of the coil, wherein for a particular one of the generated electromagnetic waveforms the digitized output of the coil is the digitized returned electromagnetic waveform.

9. A medical device identifier, comprising:
a housing;
a printed circuit board within the housing;
control electronics mounted on the printed circuit board; and
a coil positioned away from the printed circuit board and coupled to the printed circuit board for generating a sequence of electromagnetic waveforms to prompt a return signal from a medical device;
wherein the control electronics identifies the medical device based on the return signal, and wherein the control electronics further comprise:
a computer subsystem comprising a processor and memory, the memory holding instructions executable by the processor and holding a plurality of digital templates corresponding to different medical devices;
drive circuitry coupled to the coil and the computer subsystem; and
receiver circuitry coupled to the coil and the computer subsystem;
wherein the instructions, when executed by the processor, cause the medical device identifier to:
sequentially excite the coil via the drive circuitry to generate electromagnetic waveforms corresponding to a plurality of digitally predefined waveforms;
receive and digitize via the coil and the receiver circuitry a returned electromagnetic waveform transmitted from a medical device in response to the electromagnetic waveforms; and
perform a cross correlation of the digitized returned electromagnetic wave form with at least one of the plurality of digital templates.

10. The medical device identifier of claim 9, wherein the coil is coupled to the printed circuit board via a cable.

11. The medical device identifier of claim 9, wherein the coil is mounted in a portion that extends from the housing.

12. The medical device identifier of claim 9, wherein the instructions, when executed by the processor, cause the medical device identifier to:
perform a cross correlation of the digitized electromagnetic wave form with each of at least two of the templates; and
identify the medical device based on the template best matching the digitized returned electromagnetic waveform as determined by the cross correlations.

13. The medical device identifier of claim 9, wherein the control electronics further comprise a digital-to-analog converter, and wherein the generated electromagnetic waveforms are generated in part by supplying the digitally predefined waveforms to the digital-to-analog converter.

14. A portal device, comprising:
a device identification subsystem configured to identify, from a plurality of possible providers, the provider of a medical device that is in proximity to the portal device; and
a communication subsystem configured to establish two-way communication over an electronic link with a call center servicing medical devices from the identified provider;
wherein the portal device is operable to receive electromagnetic signals from the medical device, to forward to the call center information based on the electromagnetic signals received from the medical device, to receive communications from the call center carrying information to be transmitted to the medical device, and to transmit further electromagnetic signals to the medical device based on the communications received from the call center.

15. The portal device of claim 14, further comprising a plurality of translation modules corresponding respectively to the plurality of possible providers.

16. The portal device of claim 15, wherein each translation module is provided by its respective one of the plurality of possible providers.

17. The portal device of claim 14, wherein the device identification subsystem further comprises:
a coil;
a computer subsystem comprising a processor and memory, the memory holding instructions executable by the processor and holding a plurality of digital templates corresponding to different medical devices;
drive circuitry coupled to the coil and the computer subsystem; and
receiver circuitry coupled to the coil and the computer subsystem;
wherein the instructions, when executed by the processor, cause the medical device identifier to:
sequentially excite the coil via the drive circuitry to generate electromagnetic waveforms corresponding to a plurality of digitally predefined waveforms;
receive and digitize via the coil and the receiver circuitry a returned electromagnetic waveform transmitted from a medical device in response to the electromagnetic waveforms; and
identify the provider of the medical device based on a comparison of the returned electromagnetic waveform with at least one of the plurality of digital templates.

18. The portal device of claim 17, wherein the device identification subsystem further comprises a digital-to-analog converter, and wherein the generated electromagnetic waveforms are generated in part by supplying the digitally predefined waveforms to the digital-to-analog converter.

* * * * *